(12) United States Patent
Jones et al.

(10) Patent No.: US 10,932,781 B2
(45) Date of Patent: Mar. 2, 2021

(54) FEATURES TO ALIGN AND CLOSE LINEAR SURGICAL STAPLER

(71) Applicant: ETHICON LLC, Guaynabo, PR (US)

(72) Inventors: Jason Jones, Cincinnati, OH (US); Michael J. Stokes, Cincinnati, OH (US); Chester O. Baxter, III, Loveland, OH (US); Andrew T. Beckman, Cincinnati, OH (US); Anil K. Nalagatla, Mason, OH (US); Robert L. Koch, Jr., Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 250 days.

(21) Appl. No.: 15/889,374

(22) Filed: Feb. 6, 2018

(65) Prior Publication Data
US 2019/0239886 A1 Aug. 8, 2019

(51) Int. Cl.
*A61B 17/072* (2006.01)
*A61B 17/11* (2006.01)
(Continued)

(52) U.S. Cl.
CPC .... *A61B 17/1114* (2013.01); *A61B 17/07207* (2013.01); *A61B 17/115* (2013.01);
(Continued)

(58) Field of Classification Search
CPC ............ A61B 17/1114; A61B 17/2833; A61B 17/2841; A61B 17/07207; A61B 17/115;
(Continued)

(56) References Cited

U.S. PATENT DOCUMENTS

| 960,300 A | 6/1910 | Fischer |
| 2,154,366 A * | 4/1939 | Thomson .............. B25C 5/0285 227/126 |

(Continued)

FOREIGN PATENT DOCUMENTS

| DE | 38 19 292 C1 | 7/1989 |
| EP | 0033548 B1 | 5/1986 |

(Continued)

OTHER PUBLICATIONS

U.S. Appl. No. 15/889,363, filed Feb. 6, 2018.
(Continued)

*Primary Examiner* — Robert F Long
(74) *Attorney, Agent, or Firm* — Frost Brown Todd LLC

(57) ABSTRACT

A surgical stapler includes an anvil half and a cartridge half. The anvil half includes an anvil channel member and an anvil surface. The cartridge half releasably couples with the anvil half and includes a cartridge channel member having a distal portion that receives a staple cartridge, and a latching member coupled to the cartridge channel member and movable between open and closed positions. A resilient member is arranged at a proximal end of one of the anvil half or the cartridge half, and a projection is arranged at a proximal end of the other of the anvil half or the cartridge half. The resilient member is configured to contact and releasably couple with the projection to thereby couple the proximal end of the anvil half with the proximal end of the cartridge half while the latching member is in the open position.

20 Claims, 21 Drawing Sheets

(51) Int. Cl.
*A61B 17/28* (2006.01)
*A61B 17/115* (2006.01)
*A61B 17/00* (2006.01)

(52) U.S. Cl.
CPC ...... *A61B 17/2833* (2013.01); *A61B 17/2841* (2013.01); *A61B 2017/00477* (2013.01); *A61B 2017/07278* (2013.01); *A61B 2017/07285* (2013.01)

(58) Field of Classification Search
CPC .. A61B 2017/07285; A61B 2017/08278; A61B 2017/00477; A61B 17/064; A61B 17/068; A41G 5/0086; A41G 5/0073; B25C 5/0292; B25C 5/0207; F16B 15/0015; C08L 67/04; C08L 2201/06
USPC .............. 227/175.1–182.1; 606/139, 219
See application file for complete search history.

(56) References Cited

U.S. PATENT DOCUMENTS

| | | | |
|---|---|---|---|
| 2,489,050 | A * | 11/1949 | Ruskin .............. B25C 5/0207 227/128 |
| 2,938,212 | A * | 5/1960 | Lerner .................. B25C 5/085 227/86 |
| 2,977,599 | A * | 4/1961 | Shlesinger, Jr. .......... B27F 7/36 227/124 |
| 3,078,465 | A | 2/1963 | Bobrov |
| 3,079,606 | A | 3/1963 | Bobrov et al. |
| 3,315,863 | A | 4/1967 | O'Dea |
| 3,317,105 | A | 5/1967 | Astafjev et al. |
| 3,490,675 | A | 1/1970 | Green et al. |
| 3,604,561 | A * | 9/1971 | Mallina ............ A61B 17/0686 206/339 |
| 4,111,206 | A | 9/1978 | Vishnevsky et al. |
| 4,127,227 | A * | 11/1978 | Green .............. A61B 17/0684 227/19 |
| 4,187,971 | A * | 2/1980 | Prew, Jr. .............. B25C 5/162 227/125 |
| 4,241,861 | A | 12/1980 | Fleischer |
| 4,290,542 | A | 9/1981 | Fedotov et al. |
| 4,411,378 | A * | 10/1983 | Warman ............ A61B 17/0684 227/19 |
| D272,851 | S | 2/1984 | Green et al. |
| D272,852 | S | 2/1984 | Green et al. |
| 4,429,695 | A | 2/1984 | Green |
| 4,506,819 | A * | 3/1985 | Rand .................. B25C 5/1689 227/120 |
| 4,520,817 | A | 6/1985 | Green |
| 4,596,351 | A | 6/1986 | Fedotov et al. |
| 4,605,001 | A * | 8/1986 | Rothfuss .......... A61B 17/07207 227/178.1 |
| D285,836 | S | 9/1986 | Hunt et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,749,114 | A * | 6/1988 | Green .................... A61B 17/11 227/19 |
| 4,869,415 | A * | 9/1989 | Fox ................ A61B 17/07207 227/19 |
| 4,887,756 | A * | 12/1989 | Puchy .............. A61B 17/0644 227/19 |
| 4,892,244 | A | 1/1990 | Fox et al. |
| 4,955,898 | A | 9/1990 | Matsutani et al. |
| 4,955,959 | A * | 9/1990 | Tompkins ........ A61B 17/07207 227/178.1 |
| 5,065,929 | A | 11/1991 | Schulze et al. |
| 5,083,695 | A | 1/1992 | Foslien et al. |
| 5,117,557 | A * | 6/1992 | Hartley .................. A01G 3/02 30/134 |
| 5,129,570 | A | 7/1992 | Schulze et al. |
| 5,141,144 | A | 8/1992 | Foslien et al. |
| 5,156,614 | A | 10/1992 | Green et al. |
| 5,173,133 | A | 12/1992 | Morin et al. |
| 5,221,036 | A | 6/1993 | Takase |
| 5,253,793 | A * | 10/1993 | Green .............. A61B 17/07207 227/178.1 |
| 5,417,361 | A | 5/1995 | Williamson, IV |
| 5,445,304 | A | 8/1995 | Plyley et al. |
| 5,452,837 | A | 9/1995 | Williamson, IV et al. |
| 5,465,896 | A | 11/1995 | Allen et al. |
| 5,489,058 | A | 2/1996 | Plyley et al. |
| 5,505,363 | A | 4/1996 | Green et al. |
| 5,535,935 | A | 7/1996 | Vidal et al. |
| 5,542,594 | A | 8/1996 | McKean et al. |
| 5,562,241 | A | 10/1996 | Knodel et al. |
| 5,586,711 | A | 12/1996 | Plyley et al. |
| 5,636,779 | A * | 6/1997 | Palmer .................. A61B 17/072 227/175.2 |
| 5,651,491 | A | 7/1997 | Heaton et al. |
| 5,653,373 | A | 8/1997 | Green et al. |
| 5,655,698 | A | 8/1997 | Yoon |
| 5,657,921 | A | 8/1997 | Young et al. |
| 5,673,842 | A | 10/1997 | Bittner et al. |
| 5,680,983 | A * | 10/1997 | Plyley .............. A61B 17/07207 227/175.3 |
| 5,715,988 | A * | 2/1998 | Palmer ............ A61B 17/07207 227/175.3 |
| 5,718,359 | A | 2/1998 | Palmer et al. |
| 5,785,232 | A * | 7/1998 | Vidal .............. A61B 17/07207 227/176.1 |
| 5,797,538 | A * | 8/1998 | Heaton ............ A61B 17/07207 227/176.1 |
| 5,816,471 | A | 10/1998 | Plyley et al. |
| 5,871,135 | A | 2/1999 | Williamson, IV et al. |
| 5,893,506 | A * | 4/1999 | Powell .................. A61B 17/072 227/175.1 |
| 5,908,427 | A | 6/1999 | McKean et al. |
| 5,988,479 | A | 11/1999 | Palmer |
| 6,010,054 | A * | 1/2000 | Johnson ............ A61B 17/07207 227/176.1 |
| 6,045,560 | A | 4/2000 | McKean et al. |
| 6,131,789 | A | 10/2000 | Schulze et al. |
| 6,152,347 | A * | 11/2000 | Wilson .................... B25C 5/025 227/120 |
| 6,155,473 | A | 12/2000 | Tompkins et al. |
| 6,206,903 | B1 | 3/2001 | Ramans |
| 6,370,780 | B1 * | 4/2002 | Robertson ............... B26B 13/00 30/261 |
| 6,494,356 | B1 * | 12/2002 | Frank ...................... B25C 5/025 227/120 |
| 7,032,799 | B2 | 4/2006 | Viola et al. |
| 7,055,730 | B2 * | 6/2006 | Ehrenfels ......... A61B 17/07207 227/175.4 |
| 7,121,446 | B2 | 10/2006 | Arad et al. |
| 7,140,527 | B2 | 11/2006 | Ehrenfels et al. |
| 7,188,758 | B2 | 3/2007 | Viola et al. |
| 7,207,471 | B2 | 4/2007 | Heinrich et al. |
| 7,210,609 | B2 | 5/2007 | Leiboff et al. |
| 7,238,195 | B2 | 7/2007 | Viola |
| 7,278,563 | B1 | 10/2007 | Green |
| 7,293,685 | B2 | 11/2007 | Ehrenfels et al. |
| 7,326,232 | B2 | 2/2008 | Viola et al. |
| 7,334,717 | B2 | 2/2008 | Rethy et al. |
| 7,407,078 | B2 | 8/2008 | Shelton, IV et al. |
| 7,419,081 | B2 | 9/2008 | Ehrenfels et al. |
| 7,422,139 | B2 | 9/2008 | Shelton, IV et al. |
| 7,431,730 | B2 | 10/2008 | Viola |
| 7,472,815 | B2 | 1/2009 | Shelton, IV et al. |
| 7,472,816 | B2 | 1/2009 | Holsten et al. |
| 7,490,749 | B2 | 2/2009 | Schall et al. |
| 7,543,729 | B2 | 6/2009 | Ivanko |
| 7,568,604 | B2 | 8/2009 | Ehrenfels et al. |
| 7,571,845 | B2 | 8/2009 | Viola |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,637,410 | B2 | 12/2009 | Marczyk |
| 7,641,091 | B2 | 1/2010 | Olson et al. |
| 7,665,647 | B2 | 2/2010 | Shelton, IV et al. |

(56) References Cited

U.S. PATENT DOCUMENTS

| | | | |
|---|---|---|---|
| 7,717,312 B2 | 5/2010 | Beetel | |
| 7,721,933 B2 | 5/2010 | Ehrenfels et al. | |
| 7,722,610 B2 | 5/2010 | Viola et al. | |
| 7,740,160 B2 | 6/2010 | Viola | |
| 7,744,628 B2 | 6/2010 | Viola | |
| 7,766,209 B2 | 8/2010 | Baxter, III et al. | |
| 7,810,691 B2 | 10/2010 | Boyden et al. | |
| 7,815,092 B2 | 10/2010 | Whitman et al. | |
| 7,828,189 B2 | 11/2010 | Holsten et al. | |
| 7,837,081 B2 | 11/2010 | Holsten et al. | |
| 7,866,528 B2 | 1/2011 | Olson et al. | |
| 7,905,381 B2 | 3/2011 | Baxter, III et al. | |
| 7,931,182 B2 | 4/2011 | Boyden et al. | |
| 7,942,300 B2 | 5/2011 | Rethy et al. | |
| 7,954,685 B2 | 6/2011 | Viola | |
| 7,954,686 B2 | 6/2011 | Baxter, III et al. | |
| 7,997,469 B2 | 8/2011 | Olson et al. | |
| 8,006,888 B2 | 8/2011 | Viola | |
| 8,028,884 B2 | 10/2011 | Sniffin et al. | |
| 8,070,035 B2 | 12/2011 | Holsten et al. | |
| 8,074,861 B2 | 12/2011 | Ehrenfels et al. | |
| 8,091,754 B2 | 1/2012 | Ehrenfels et al. | |
| 8,113,407 B2 | 2/2012 | Holsten et al. | |
| 8,127,975 B2 | 3/2012 | Olson et al. | |
| 8,152,041 B2 | 4/2012 | Kostrzewski | |
| 8,157,153 B2 | 4/2012 | Shelton, IV et al. | |
| 8,231,040 B2 | 7/2012 | Zemlok et al. | |
| 8,245,901 B2 | 8/2012 | Stopek | |
| 8,256,655 B2 | 9/2012 | Sniffin et al. | |
| 8,257,634 B2 | 9/2012 | Scirica | |
| 8,267,300 B2 | 9/2012 | Boudreaux | |
| 8,272,552 B2 | 9/2012 | Holsten et al. | |
| 8,292,146 B2 | 10/2012 | Holsten et al. | |
| 8,292,148 B2 | 10/2012 | Viola | |
| 8,308,043 B2 | 11/2012 | Bindra et al. | |
| 8,336,753 B2 | 12/2012 | Olson et al. | |
| 8,348,129 B2 | 1/2013 | Bedi et al. | |
| 8,418,907 B2 | 4/2013 | Johnson et al. | |
| 8,464,922 B2 | 6/2013 | Marczyk | |
| 8,496,154 B2 | 7/2013 | Marczyk et al. | |
| 8,496,156 B2 | 7/2013 | Sniffin et al. | |
| 8,496,683 B2 | 7/2013 | Prommersberger et al. | |
| 8,505,801 B2 | 8/2013 | Ehrenfels et al. | |
| 8,544,712 B2 | 10/2013 | Jankowski | |
| 8,579,178 B2 | 11/2013 | Holsten et al. | |
| 8,636,193 B2 | 1/2014 | Whitman et al. | |
| 8,636,939 B2 | 1/2014 | Czernik et al. | |
| 8,679,156 B2 | 3/2014 | Smith et al. | |
| 8,708,210 B2 | 4/2014 | Zemlok et al. | |
| 8,728,118 B2 | 5/2014 | Hinman et al. | |
| 8,789,740 B2 | 7/2014 | Baxter, III et al. | |
| 8,905,287 B2 | 12/2014 | Racenet et al. | |
| 8,915,930 B2 | 12/2014 | Huitema et al. | |
| 9,016,541 B2 | 4/2015 | Viola et al. | |
| 9,119,617 B2 | 9/2015 | Souls et al. | |
| 9,364,219 B2 | 6/2016 | Olson et al. | |
| 9,402,629 B2 | 8/2016 | Ehrenfels et al. | |
| 9,439,649 B2 | 9/2016 | Shelton, IV et al. | |
| 9,451,959 B2 | 9/2016 | Patankar et al. | |
| 9,474,525 B2 | 10/2016 | Smith et al. | |
| 9,498,213 B2 | 11/2016 | Marczyk et al. | |
| 9,561,030 B2 | 2/2017 | Zhang et al. | |
| 9,629,812 B2 | 4/2017 | Widenhouse et al. | |
| 9,636,113 B2 | 5/2017 | Wenchell | |
| 9,636,128 B2 | 5/2017 | Zemlok et al. | |
| 9,681,873 B2 | 6/2017 | Smith et al. | |
| 9,693,775 B2 | 7/2017 | Agarwal et al. | |
| 9,750,502 B2 | 9/2017 | Scirica et al. | |
| 9,867,616 B2 | 1/2018 | Marczyk | |
| 9,987,007 B2 * | 6/2018 | Kapadia | A61B 17/07207 |
| 2003/0042286 A1 * | 3/2003 | Yoshie | B27F 7/36 227/130 |
| 2004/0020669 A1 * | 2/2004 | Spielmann | B25F 5/001 173/178 |
| 2006/0180633 A1 | 8/2006 | Emmons | |
| 2007/0119901 A1 | 5/2007 | Ehrenfels et al. | |
| 2007/0145096 A1 | 6/2007 | Viola et al. | |
| 2007/0187451 A1 * | 8/2007 | Chang | B25C 5/0292 227/129 |
| 2009/0255974 A1 | 10/2009 | Viola | |
| 2009/0308907 A1 | 12/2009 | Nalagatla et al. | |
| 2010/0133317 A1 | 6/2010 | Shelton, IV et al. | |
| 2011/0147021 A1 * | 6/2011 | Schaal | B25D 16/00 173/47 |
| 2011/0290856 A1 | 12/2011 | Shelton, IV et al. | |
| 2012/0046689 A1 | 2/2012 | Criscuolo et al. | |
| 2012/0286022 A1 | 11/2012 | Olson et al. | |
| 2013/0186935 A1 | 7/2013 | Edoga et al. | |
| 2013/0190732 A1 | 7/2013 | Slisz et al. | |
| 2013/0264370 A1 * | 10/2013 | Chen | A61B 17/072 227/175.2 |
| 2014/0103091 A1 | 4/2014 | Whitman et al. | |
| 2015/0327855 A1 | 11/2015 | Katre et al. | |
| 2016/0157890 A1 | 6/2016 | Drake et al. | |
| 2016/0262756 A1 * | 9/2016 | Patankar | A61B 17/07207 |
| 2017/0095251 A1 * | 4/2017 | Thompson | A61B 17/3468 |
| 2018/0055512 A1 | 3/2018 | Stokes et al. | |
| 2020/0046351 A1 * | 2/2020 | Jones | A61B 17/072 |
| 2020/0046353 A1 * | 2/2020 | Deck | A61B 17/07207 |

FOREIGN PATENT DOCUMENTS

| | | |
|---|---|---|
| EP | 0178940 B1 | 1/1991 |
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2013/109445 A2 | 7/2013 |
| WO | WO 2015/065485 A1 | 5/2015 |

OTHER PUBLICATIONS

U.S. Appl. No. 15/889,370, filed Feb. 6, 2018.
U.S. Appl. No. 15/889,376, filed Feb. 6, 2018.
U.S. Appl. No. 15/889,388, filed Feb. 6, 2018.
U.S. Appl. No. 15/889,390, filed Feb. 6, 2018.
European Search Report, Extended, and Written Opinion dated May 10, 2019 for Application No. EP 19155457.5, 8 pgs.
International Search Report and Written Opinion dated Jul. 3, 2019 for Application No. PCT/IB2019/050358, 12 pgs.

* cited by examiner

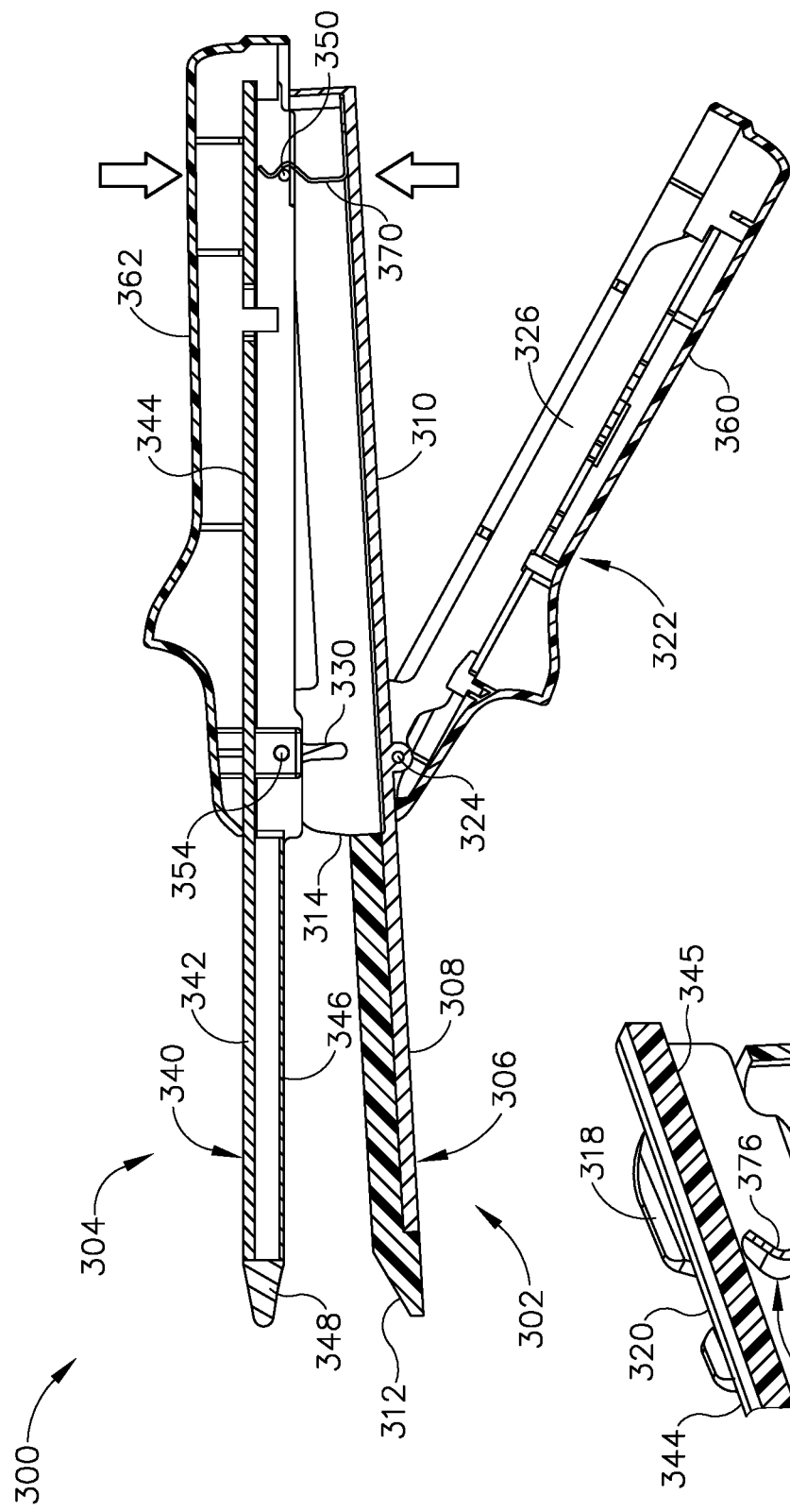
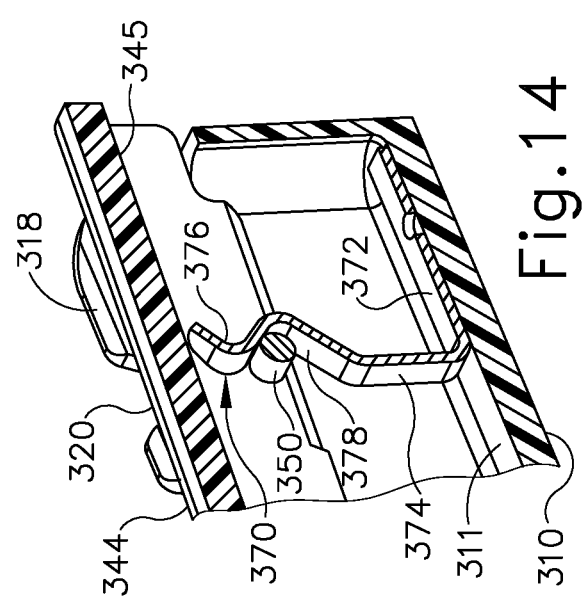

FEATURES TO ALIGN AND CLOSE LINEAR SURGICAL STAPLER

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. Typically, the first jaw and the second jaw may pivot relative each other in order to grasp tissue between the jaws. Staples are arranged in the staple cartridge such that a portion of firing assembly may actuate through the staple cartridge to drive staples out of staple cartridge, through tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13B depicts a cross-sectional side view of the surgical stapling instrument of FIG. 13A, showing the instrument halves coupled together in an open position in which a resilient retaining member of the cartridge half releasably captures a pivot pin of the anvil half;

FIG. 14 depicts an enlarged cross-sectional perspective view of a proximal end of the surgical stapling instrument of FIG. 13B, showing the resilient retaining member of the cartridge half in releasable engagement with the pivot pin of the anvil half;

Figure 1:
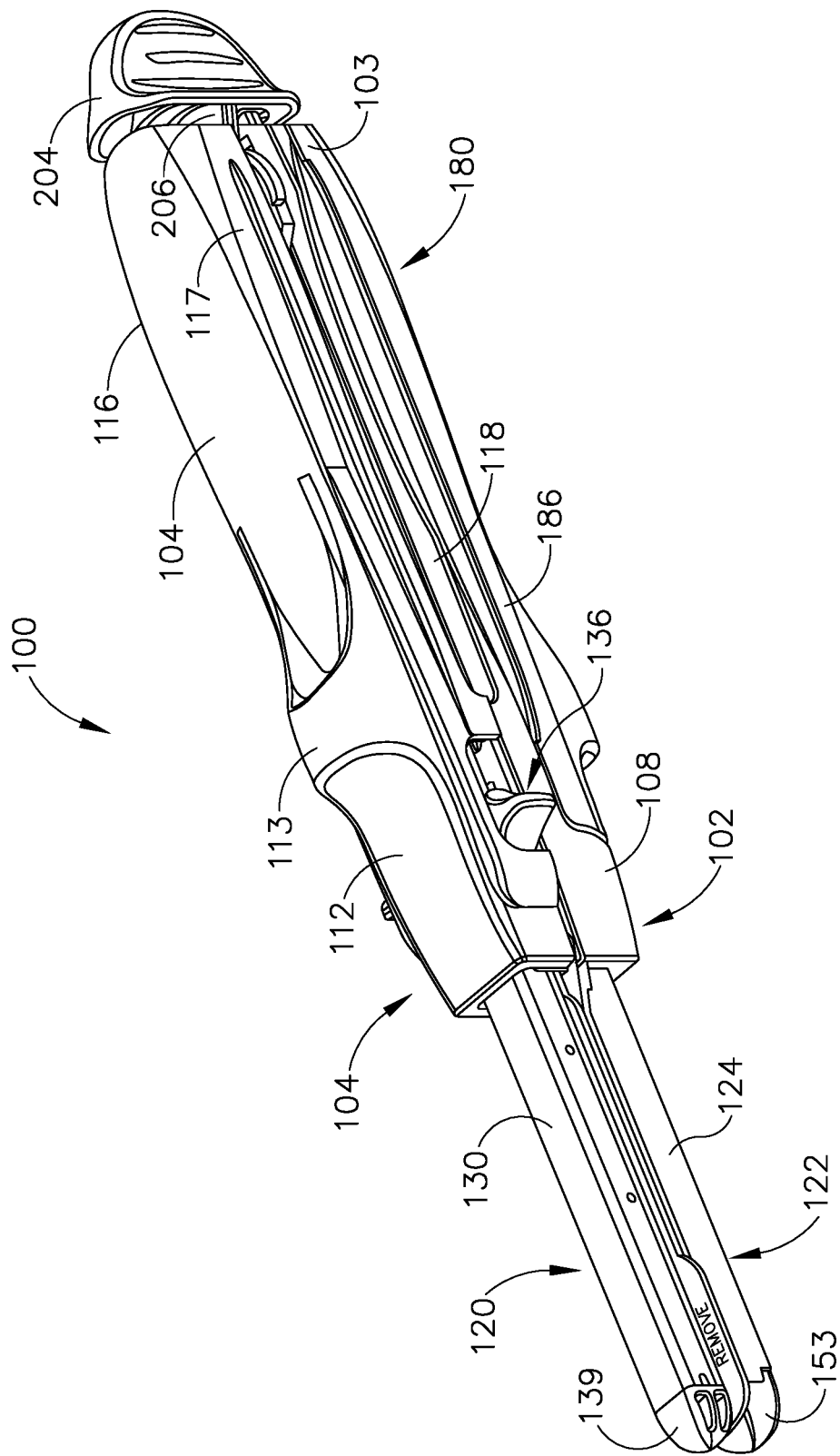
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. Exemplary Linear Cutting Stapler

A. Overview of Features of Linear Cutting Stapler

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160) housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
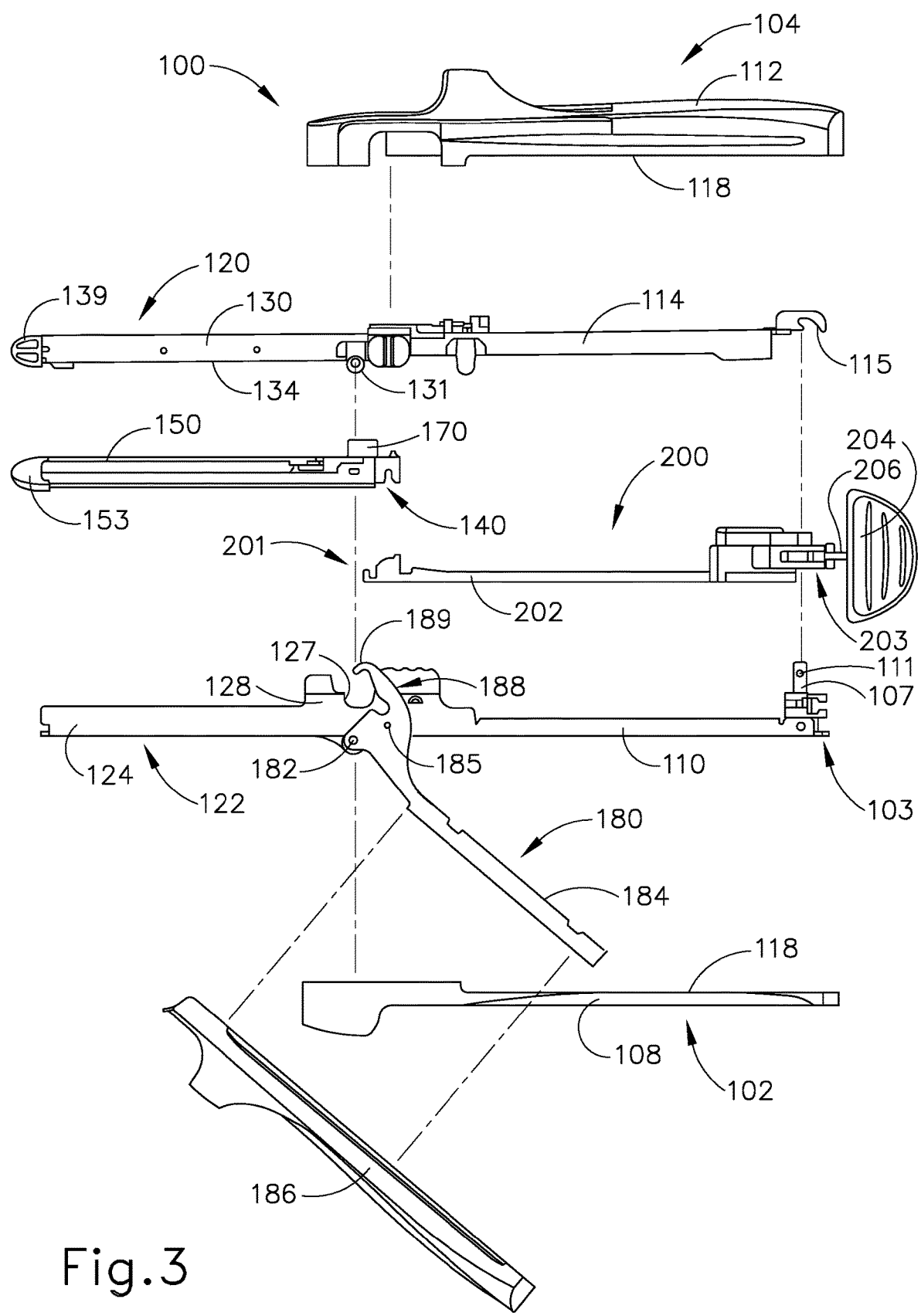
FIG. 3 depicts an exploded elevational side view of the surgical stapling instrument of FIG. 1.

As seen in FIG. 3, first portion (102) includes a first proximal frame (110), staple cartridge channel (122), and a latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
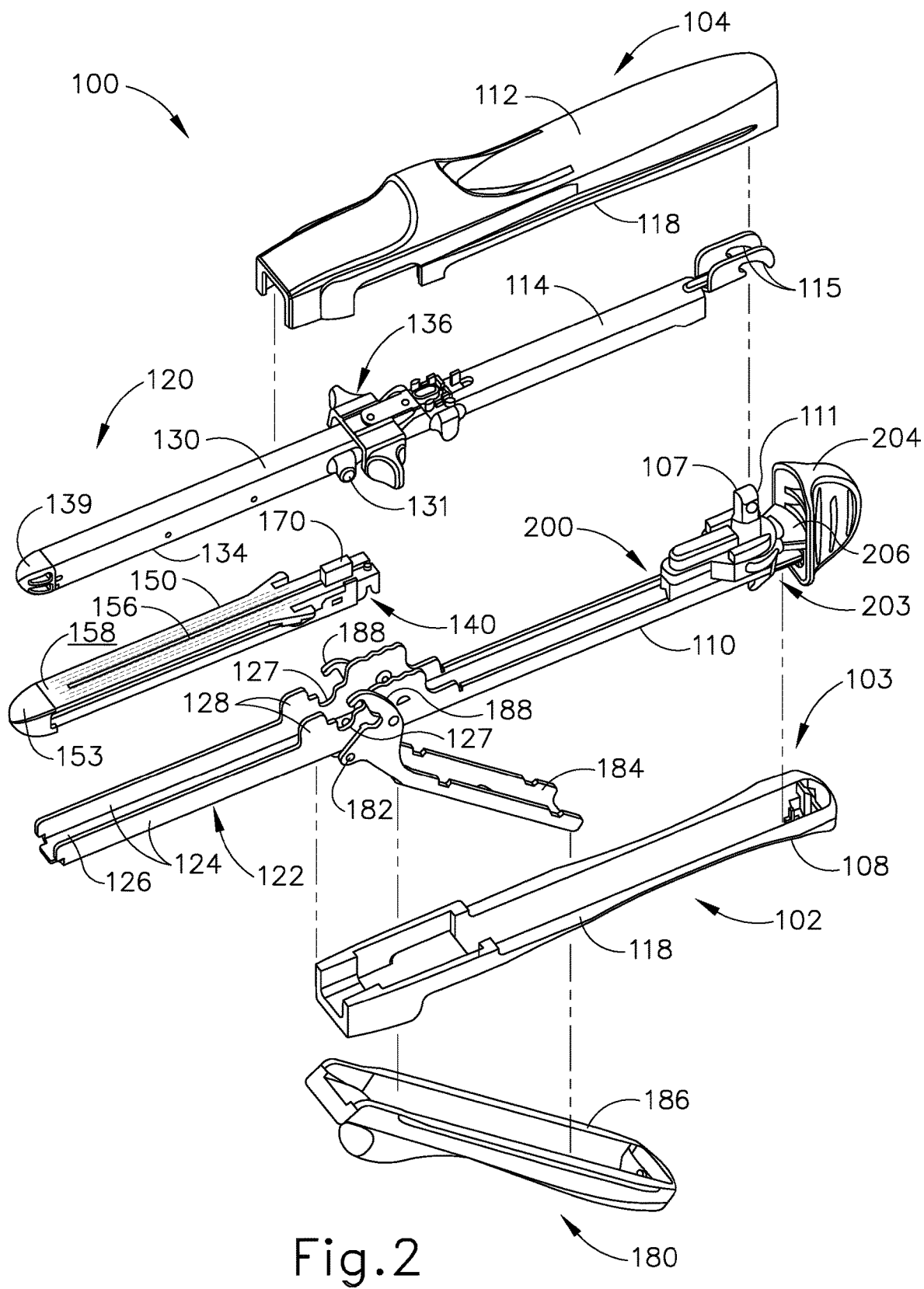
FIG. 2 depicts an exploded perspective view of the surgical stapling instrument of FIG. 1.
Figure 4:
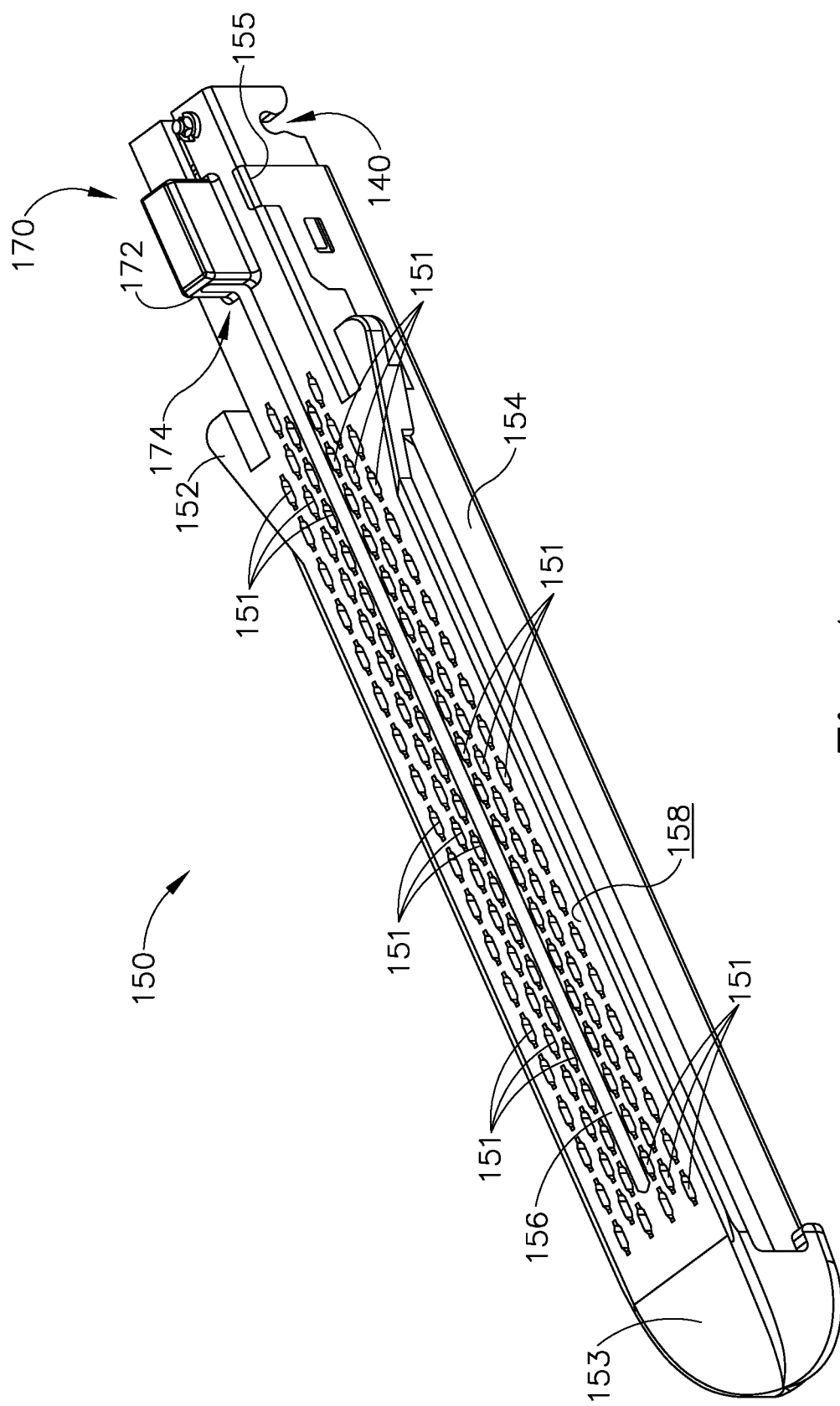
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189) (or "jaws"). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
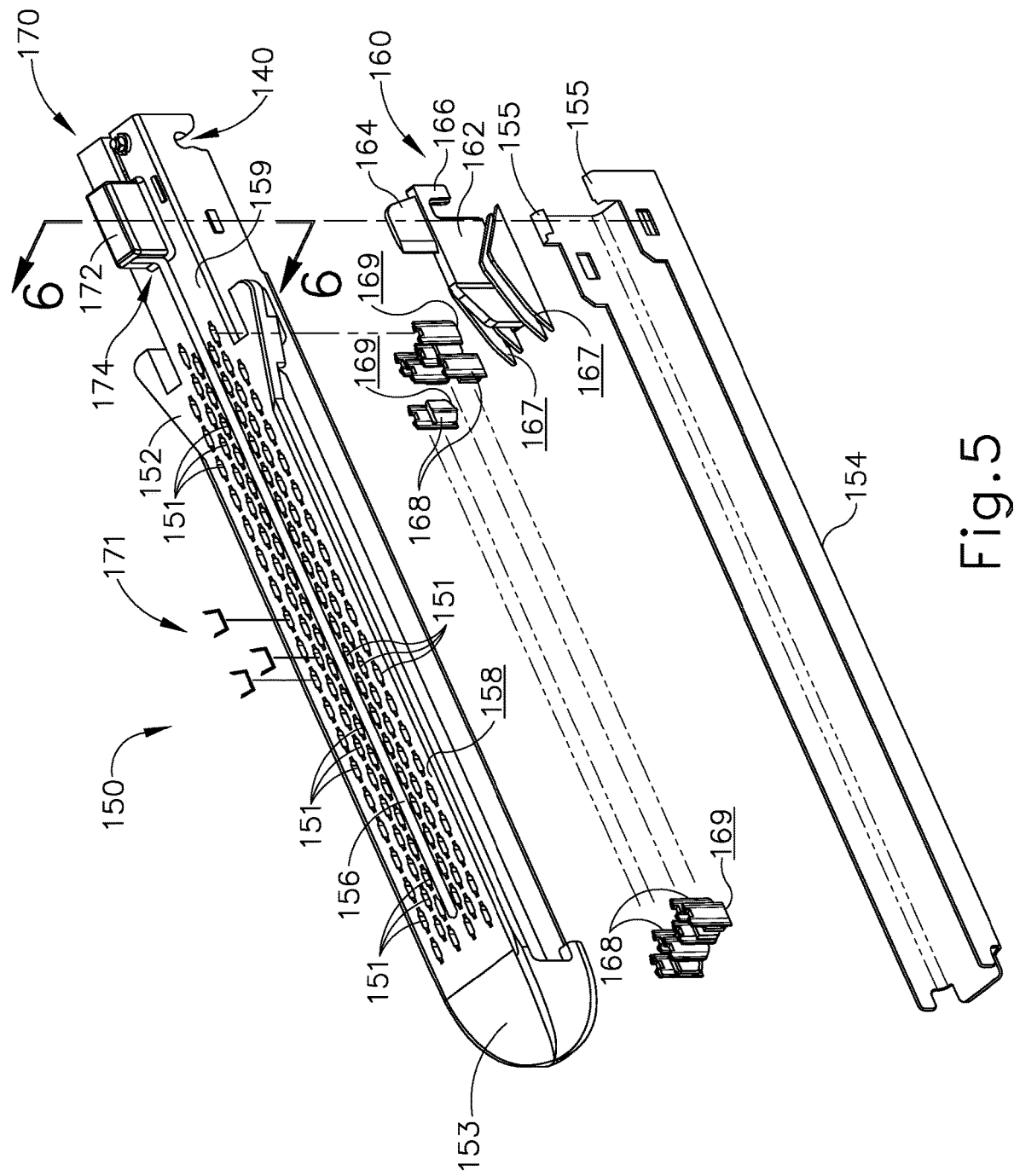
FIG. 5 depicts an exploded view of the staple cartridge assembly of FIG. 4.
Figure 6:
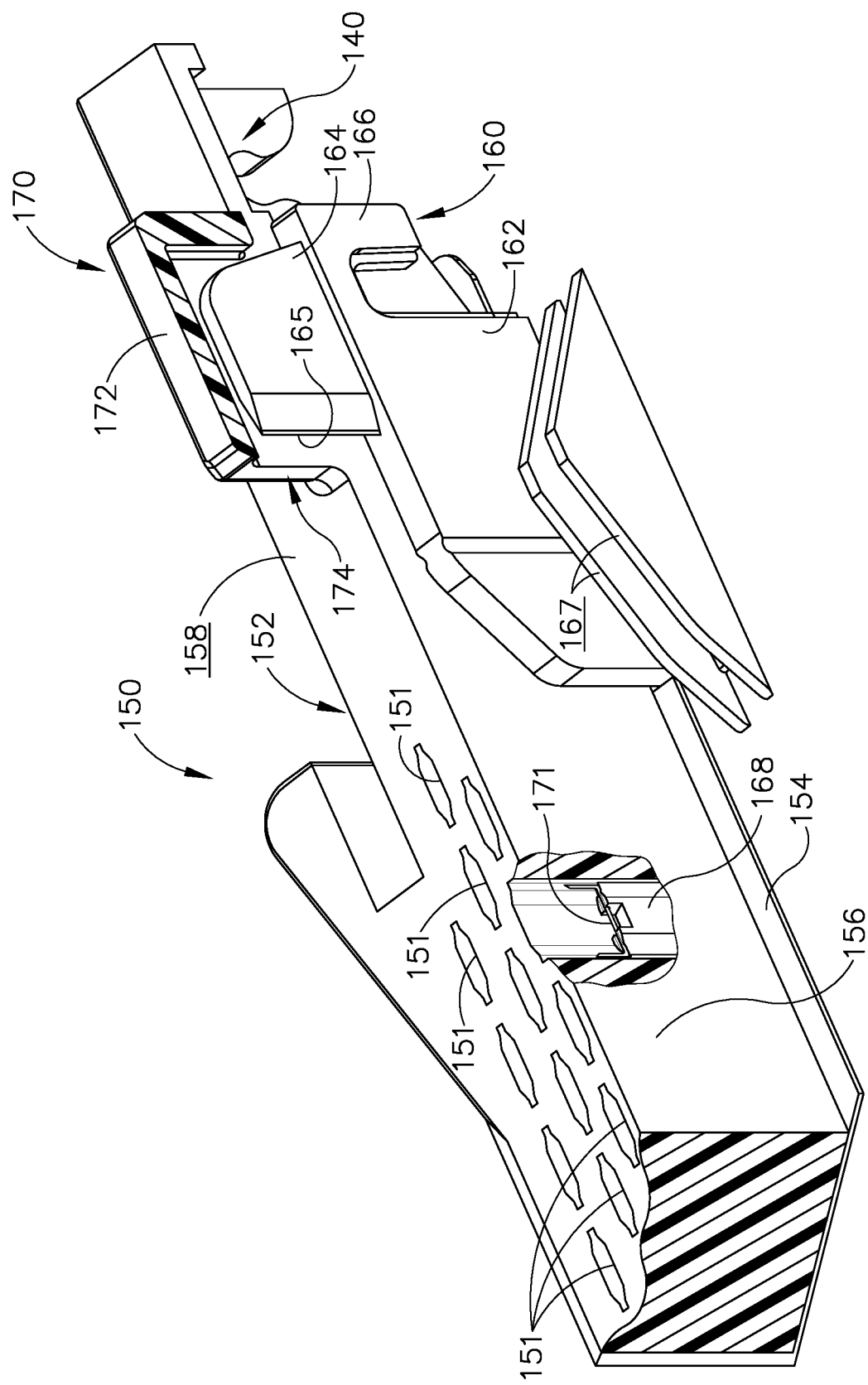
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (171). Cartridge body (152) defines a plurality of staple cavities (151), a slot (156), and coupling cutouts (140). Staple drivers (168) and respective staples (171) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (171). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (171) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

Figures 7, 8:
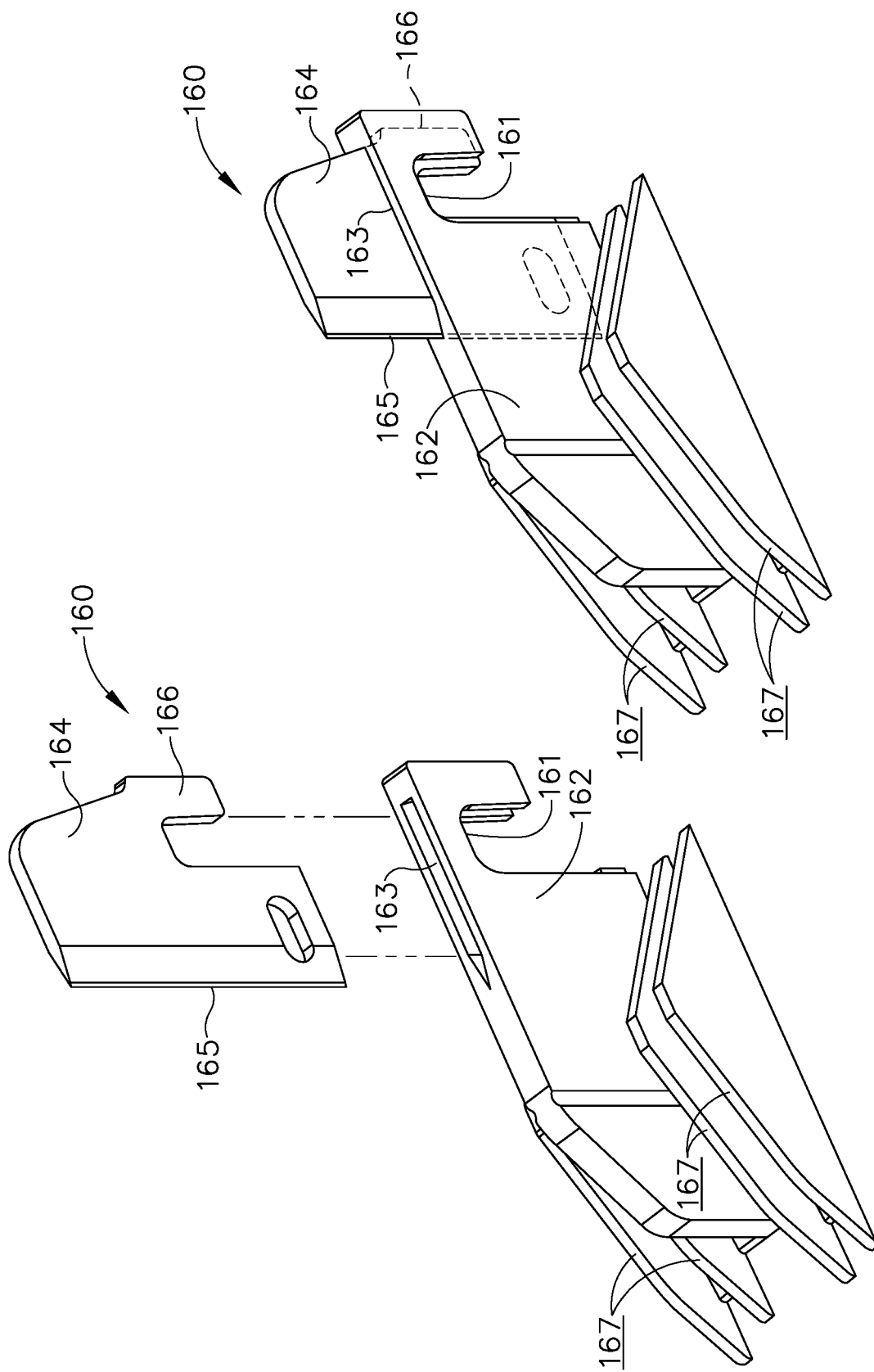
FIG. 7 depicts an exploded view of a staple sled assembly of the surgical stapling instrument of FIG. 1.
FIG. 8 depicts a perspective view of the staple sled assembly of FIG. 7.

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner was would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surface (167) are configured to engage and cam against sloped surfaces (169) of staple drivers (168) within staple cavities (151) in order to actuate staple drivers (168) toward staple deck (158). Staple drivers (168) then drive corresponding staples (171) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil surface disposed along and supported by anvil channel (130) and shown in the form of anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Figure 9:
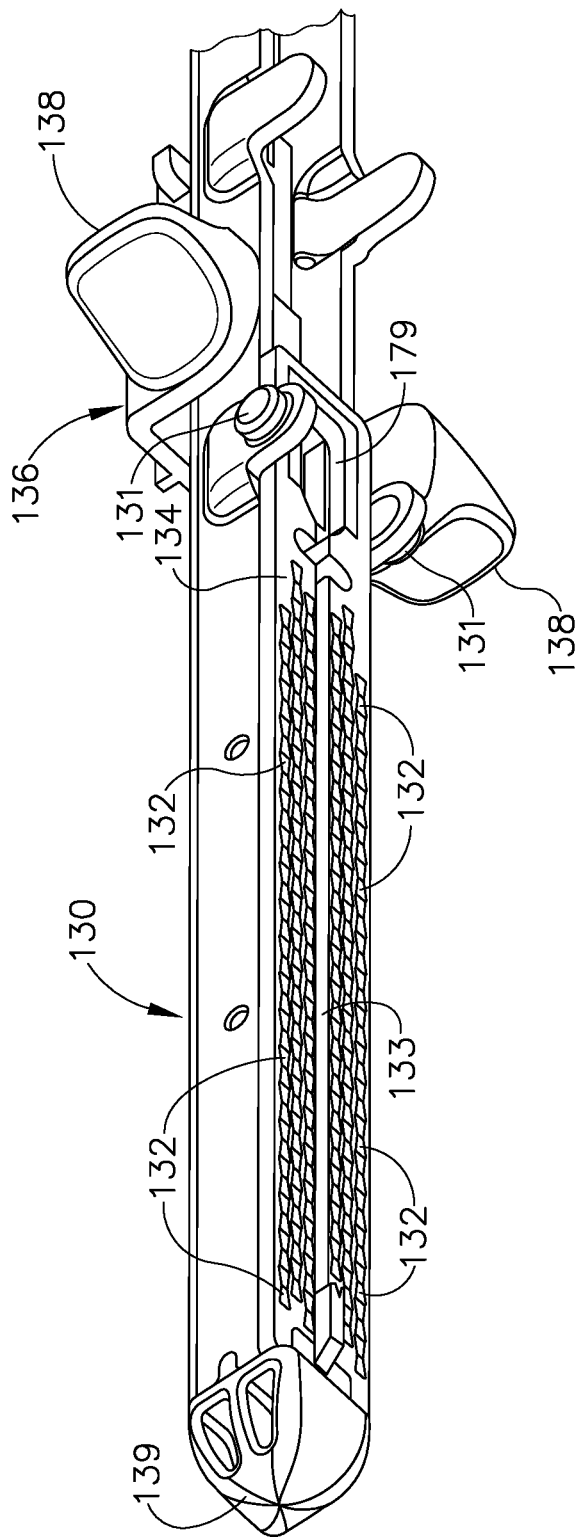
FIG. 9 depicts a perspective view of an anvil assembly of the surgical stapling instrument of FIG. 1.

Second portion (104) terminates distally in a distal nose (139). Distal nose (153) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (171) are driven through staple cavities (151) away from staple deck (158), through tissue, and against a corresponding staple forming pocket (132) such that staples (171) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil plate (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other versions. In some versions of instrument (100), the anvil surface, shown in the form of anvil plate (134), may be fixed relative to anvil channel (130). For instance, the anvil surface may be formed integrally with anvil channel (130). In such versions, it will be appreciated that the anvil surface is still "supported by" anvil channel (130).

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Cutting Stapler

Figure 10A:
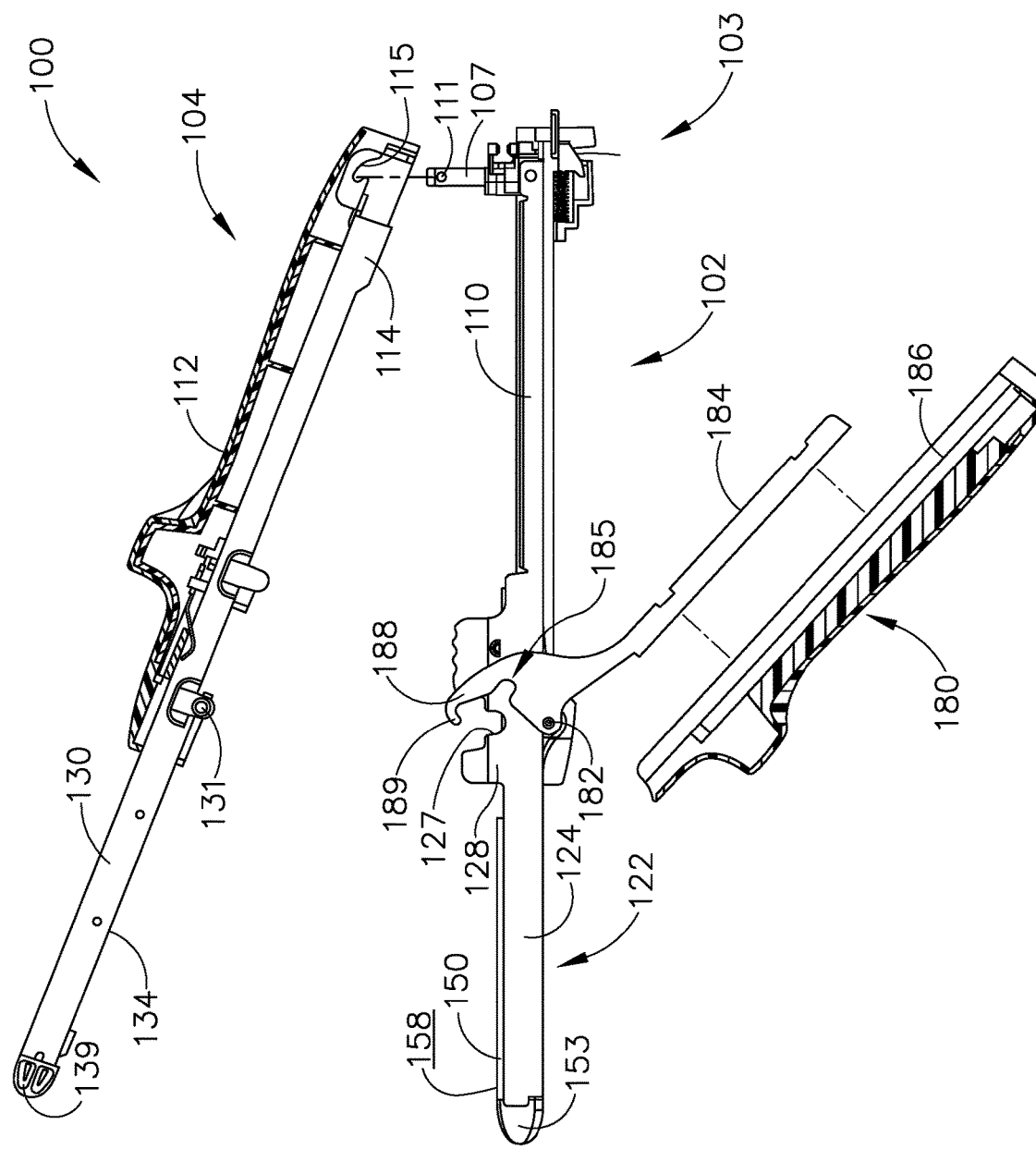
FIG. 10A depicts a cross-sectional side view of the surgical stapling instrument of FIG. 1, where a first portion and a second portion are decoupled from each other, and where an arm cover of the second portion is shown detached from the first portion for illustrative purposes.
Figure 10B:
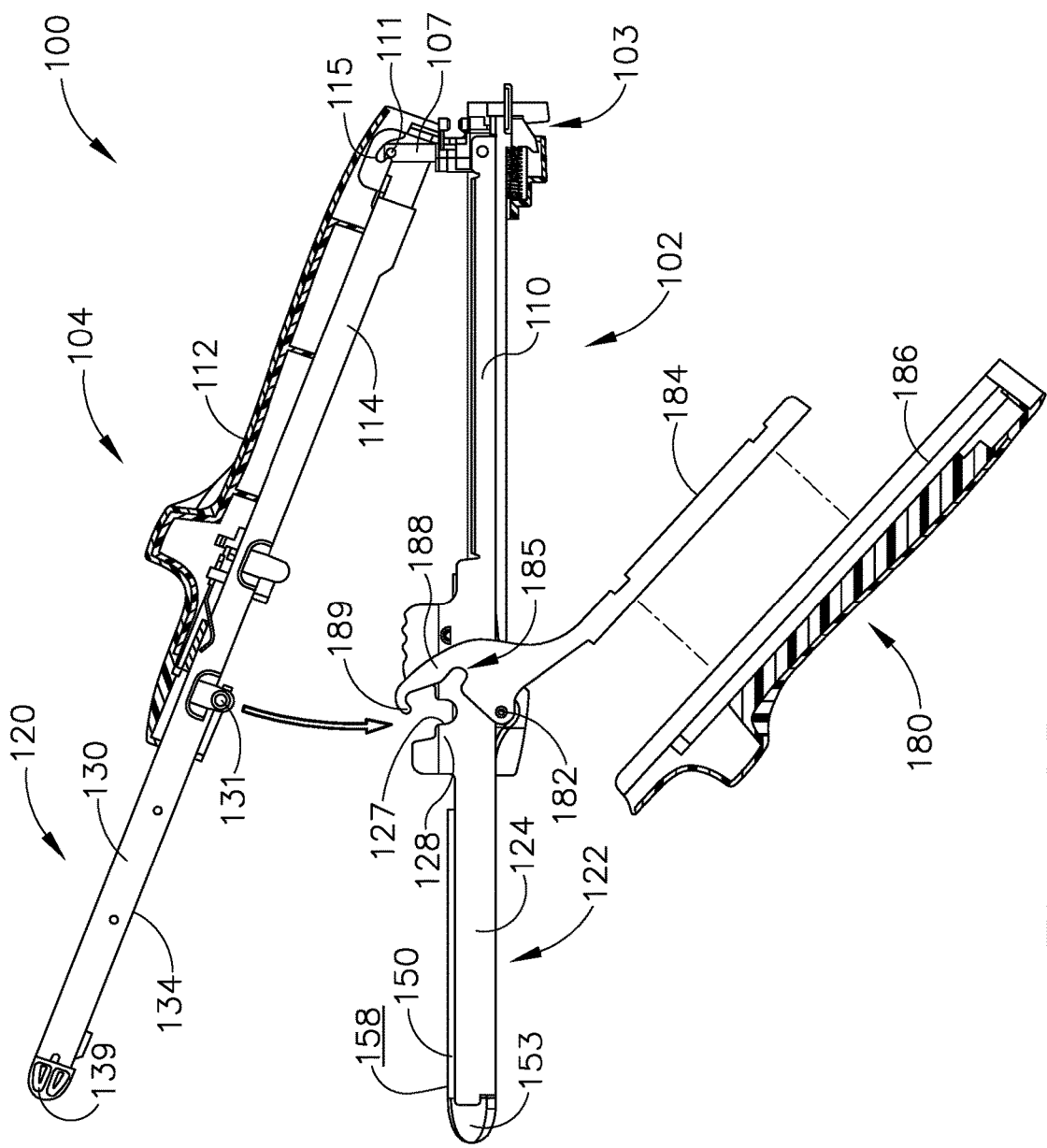
FIG. 10B depicts a cross-sectional side view of the surgical instrument of FIG. 1, where the first portion and the second portion of FIG. 10A are coupled with each other in an opened position.
Figure 10C:
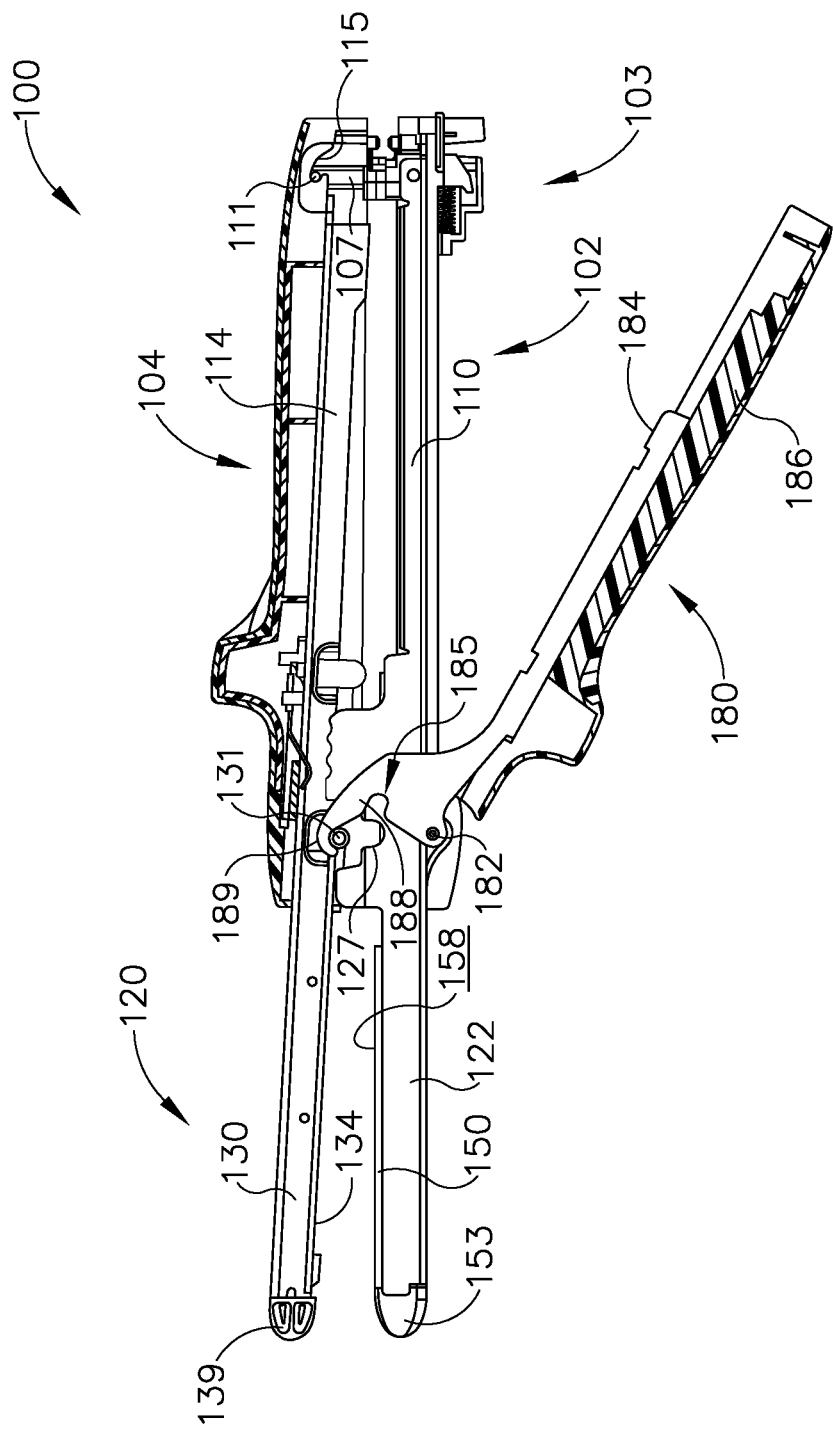
FIG. 10C depicts a cross-sectional side view of the surgical instrument of FIG. 1, where the first portion and the second portion of FIG. 10A are coupled with each other in a partially closed position.
Figure 10D:
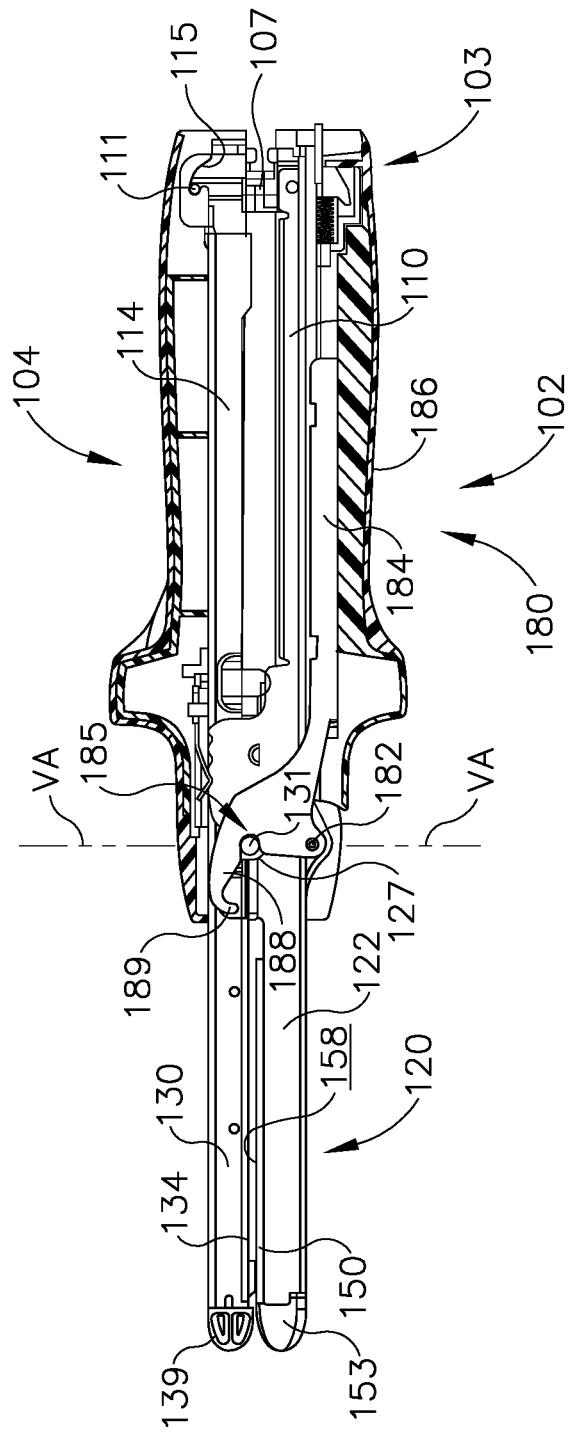
FIG. 10D depicts a cross-sectional side view of the surgical instrument of FIG. 1, where the first portion and the second portion of FIG. 10A are coupled with each other in a fully closed position.
Figure 11A:
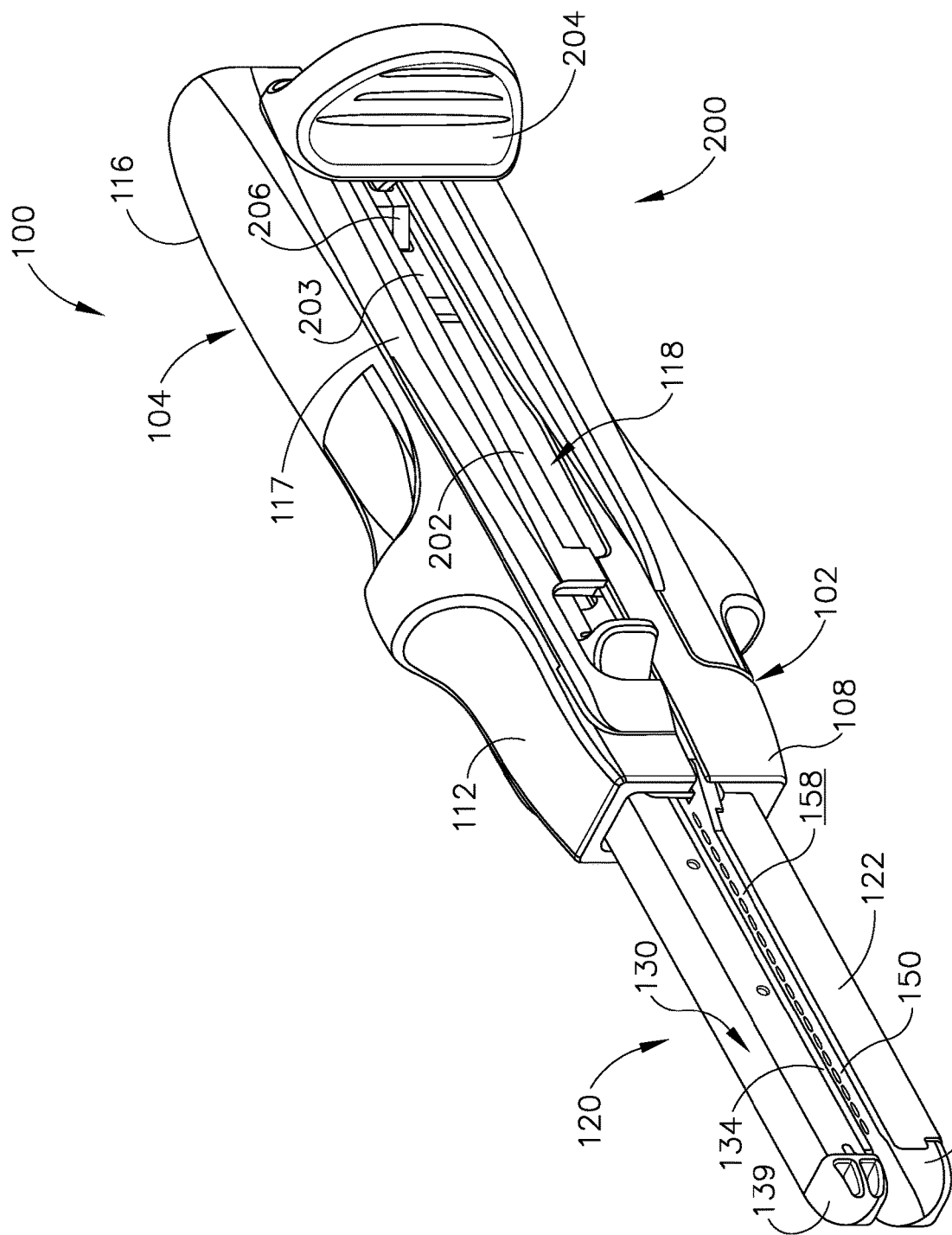
FIG. 11A depicts a perspective view of the surgical instrument of FIG. 1, where a firing assembly is in a pre-fired position.
Figure 11B:
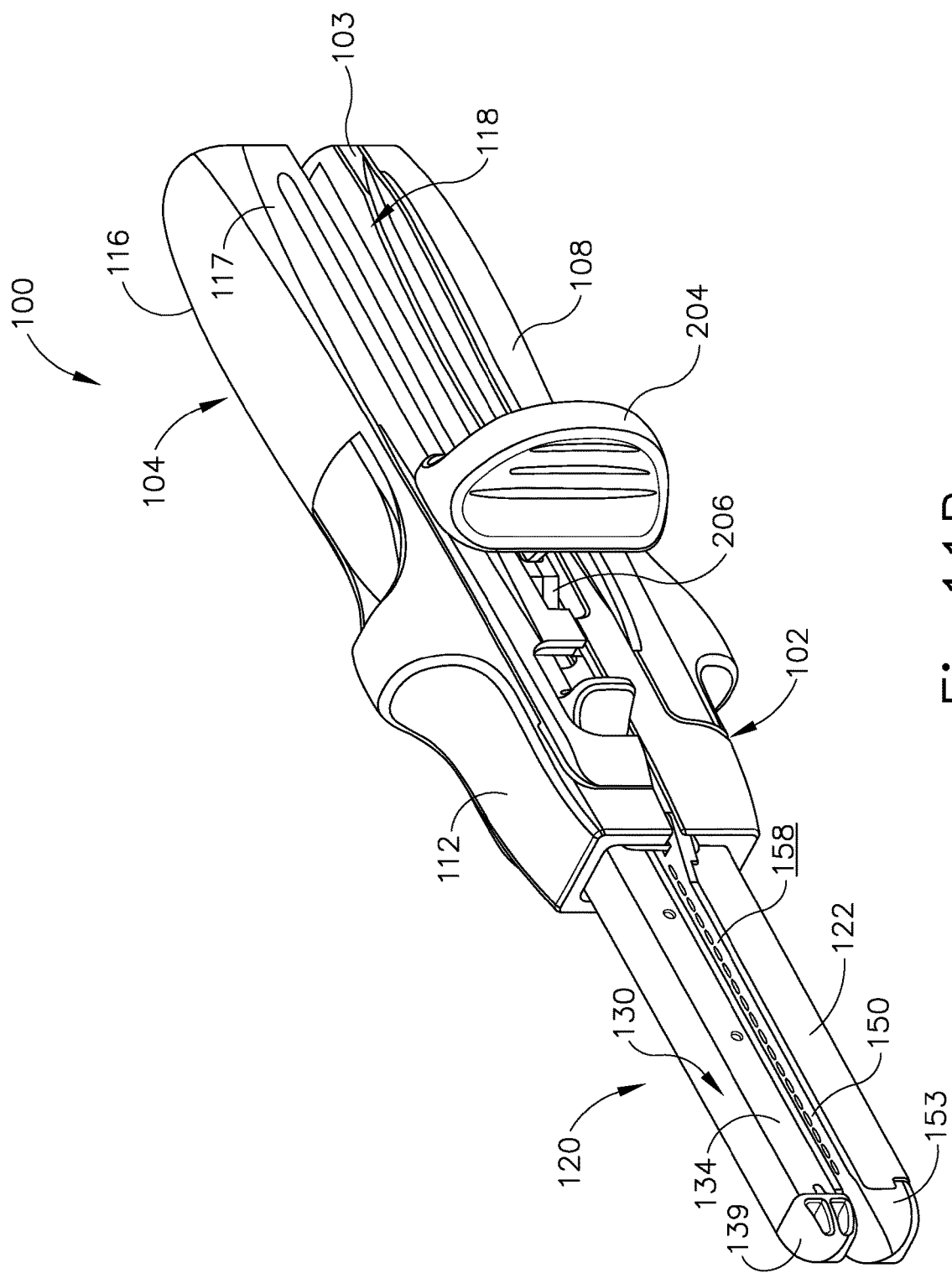
FIG. 11B depicts a perspective view of the surgical instrument of FIG. 1, where the firing assembly of FIG. 11A is in a fired position.

FIGS. 10A-11B show an exemplary use of linear cutting stapler (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102)

in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

II. Exemplary Linear Cutting Stapler Having Resilient Retaining Member

As described above in connection with FIGS. 10A-10C, the proximal ends of first and second stapler portions (102, 104) must be aligned with one another and hooks (189) of latching lever (180) must be partially coupled with latch projections (131) of second stapler portion (104) in order to place stapler (100) in a state ready for clamping tissue with end effector (120). However, this process of initially coupling together first and second stapler portions (102, 104) requires the use of both of the operator's hands, thus making it difficult to simultaneously position the tissue relative to the stapler portions (102, 104) before engaging latch projections (131). In some cases, the help of an assistant is required to facilitate this step.

In many instances, it may be desirable for the operator to position the stapler relative to tissue without the aid of an assistant, where the operator uses a first hand to hold the stapler and a second hand to position tissue relative to the stapler. The exemplary stapler (300) described below includes features that enable proximal portions of the first and second stapler halves to remain coupled together while the latching lever is in a fully open position. This configuration enables the operator to suitably manipulate the stapler relative to tissue with a first hand, while leaving the other hand free to manipulate tissue relative to the stapler.

A. Overview of Exemplary Linear Cutting Stapler

FIGS. 12-15 show another exemplary linear cutting stapler (300) that is similar to linear cutting stapler (100) except as otherwise described below. Stapler (300) includes a cartridge half (302) and an anvil half (304) configured to releasably couple together. Cartridge half (302) includes an elongate cartridge channel member (306) having a distal channel portion (308) defining a distal end of cartridge channel member (306), and a proximal frame portion (310) defining a proximal end of cartridge channel member (306). Distal channel portion (308) is configured to receive a staple cartridge (312), which may be similar to staple cartridge (150) described above. Proximal frame portion (310) is configured to slidably retain components of a firing assembly (not shown), which may be similar to firing assembly (200) described above.

Figure 13A:
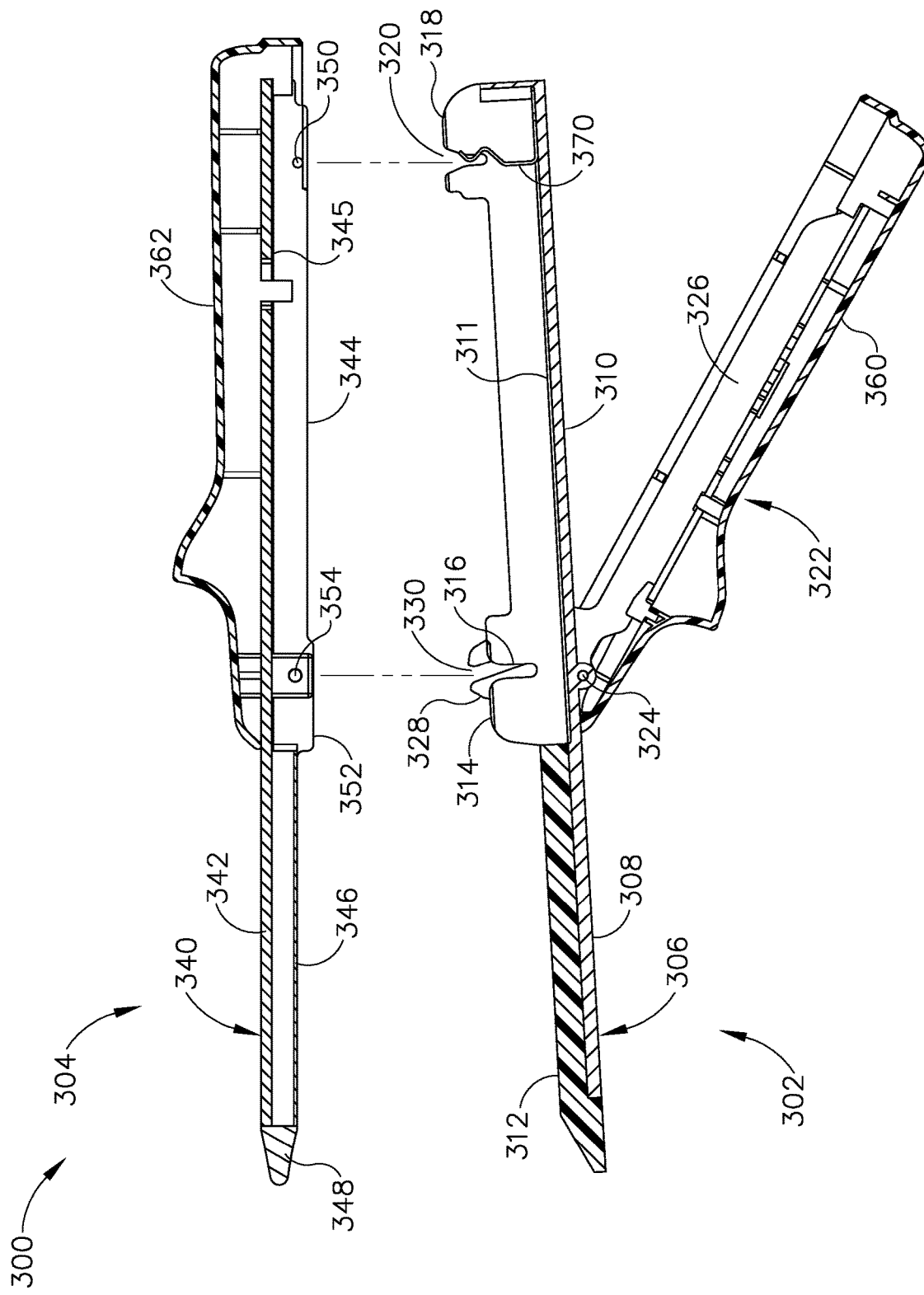
FIG. 13A depicts a cross-sectional side view of the surgical stapling instrument of FIG. 12, showing an anvil half and a cartridge half of the instrument decoupled from one another.

As best seen in FIG. 13A, cartridge channel member (306) further includes a first pair upright side flanges (314) arranged medially between distal channel portion (308) and proximal frame portion (310). Each medial side flange (314) includes a slot (316) that extends transversely to a longitudinal axis of cartridge channel member (306) and opens to a side of cartridge half (302) that faces anvil half (304). A second pair of upright side flanges (318) are arranged at the proximal end of proximal frame portion (310). Similar to medial side flanges (314), each proximal side flange (318) includes a transversely extending slot (320) that opens to a side of cartridge half (302) that faces anvil half (304). In the present example, each proximal transverse slot (320) includes a flared opening that facilitates alignment of the proximal end of cartridge half (302) with the proximal end of anvil half (304) during coupling thereof, described below.

Figure 12:
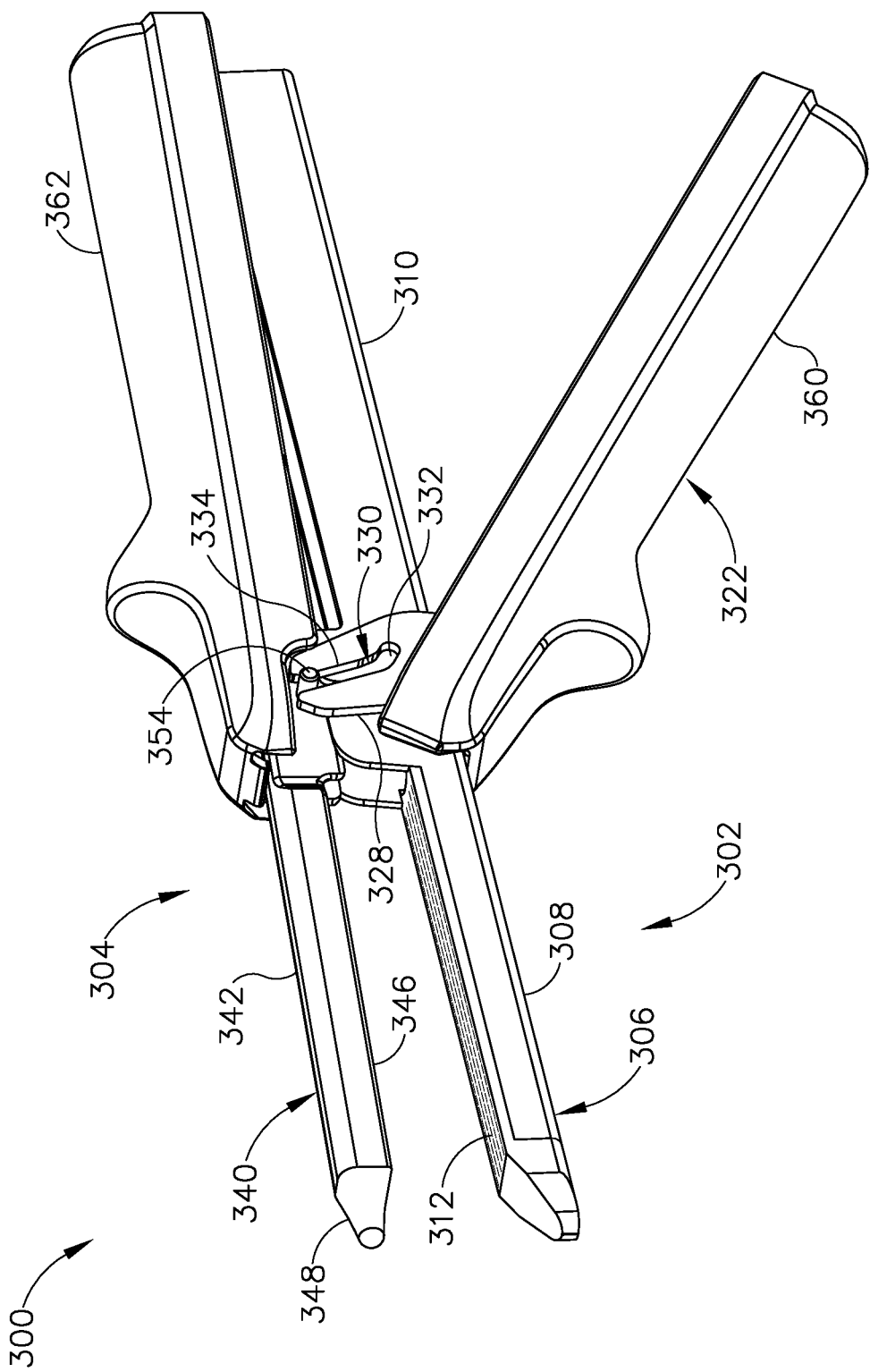
FIG. 12 depicts a perspective view of another exemplary surgical stapling instrument.

Cartridge half (302) further includes a latching lever (322) pivotably coupled to cartridge channel member (306) with a latch pivot pin (324) arranged at a medial portion of cartridge channel member (306) corresponding to medial side flanges (314). In the present example, latch pivot pin (324) is approximately aligned with transverse slots (316) of medial side flanges (314), as seen in FIG. 13A. Latching lever (322) includes an elongate lever arm (326) and a pair of opposed jaws (328) extending distally from lever arm (326) and curving towards anvil half (304), as best seen in FIG. 12. Each jaw (328) includes an elongate slot (330) configured to receive a corresponding latch projection of anvil half (304), as described below. Each jaw slot (330) has a closed proximal end and an open distal end configured to receive the corresponding latch projection. Additionally, each jaw slot (330) includes a linear proximal slot portion (332) that extends distally from the closed proximal end, and a linear distal slot portion (334) that extends distally from and angularly relative to proximal slot portion (332) and opens to the open distal end of jaw slot (330). Similar to latching lever (180) described above, latching lever (322) is configured to pivot relative to cartridge channel member (306) to selectively clamp anvil half (304) against cartridge half (302). As described below, latching lever (322) is pivotable relative to cartridge channel member (306) between an open position (see FIGS. 12-13B) in which latching lever (322) permits movement of anvil half (304) relative to cartridge half (302), and a closed position (see FIG. 15) in which latching lever (322) fixes anvil half (304) relative to cartridge half (302).

As best seen in FIG. 13A, anvil half (304) of linear cutting stapler (300) includes an elongate anvil channel member (340) having a distal channel portion (342) and a proximal frame portion (344). Distal channel portion (342) supports an anvil surface shown in the form of anvil plate (346) having a plurality of staple forming pockets (not shown) similar to pockets (132), and additionally supports a distal tip member (348) defining a distal end of anvil half (304). In other variations of stapler (300), the anvil surface may be formed integrally with or otherwise be rigidly connected to distal channel portion (342). In such variations, it will be appreciated that the anvil surface is still "supported by" distal channel portion (342). Proximal frame portion (344) defines a proximal end of anvil channel member (340), and supports a laterally extending pivot pin (350) at the proximal end. As described below, anvil channel member (340) is configured to pivot relative to cartridge channel member (306) about an axis defined by pivot pin (350). Anvil channel member (340) further includes a pair of upright side flanges (352) arranged medially between distal channel portion (342) and proximal frame portion (344). A pair of latch projections is defined by a structure shown in the form of a latch pin (354) extending laterally through side flanges (352), proximal to a proximal end of anvil plate (346). In other versions, the latch projections of stapler (300) may be similar to latch projections (131) of stapler (100).

In the present example, a first handle cover (360) is coupled to lever arm (326) of latching lever (322), and a second handle cover (362) is coupled to proximal frame portion (344) of anvil channel member (340). Though not shown, an additional cover similar to cover (108) may be coupled to proximal frame portion (310) of cartridge channel member (306). Covers (360, 362) are configured to facilitate secure gripping of stapler (300) by an operator during use. It will be appreciated that various other features of stapler (100) described above may be incorporated into stapler (300) as well.

As best seen in FIG. 14, cartridge half (302) further includes a retaining member shown in the form of an L-shaped retaining spring (370) arranged at a proximal end of cartridge half (302). As described below, retaining spring (370) is configured to contact and releasably capture pivot pin (350) of anvil half (304) to thereby couple the proximal ends of cartridge half (302) and anvil half (304) even while latching lever (322) remains in its open position, as shown in FIG. 13B. Retaining spring (370) includes a base leg (372) fixedly secured to an inner base surface (311) of cartridge channel member (306) at its proximal end, and an upright leg (374) extending perpendicularly away from base leg (372) in a direction toward anvil half (304). In the present example, upright leg (374) terminates at a free end (376) configured to confront an inner base surface (345) of anvil channel member (340) when retaining spring (370) is coupled with pivot pin (350) of anvil half (304). Additionally, upright leg (374) is positioned in alignment with proximal flange slots (320) of cartridge channel member (306).

Upright leg (374) of retaining spring (370) is provided with a bent configuration that defines a distally opening recess (378) configured to releasably receive pivot pin (350) therein. In use, upright leg (374) is configured to resiliently deflect proximally relative to its base leg (372) to thereby receive and retain pivot pin (350) within recess (378), as seen in FIG. 14, thereby releasably coupling the proximal ends of cartridge half (302) and anvil half (304). In the present example, free end (376) of upright leg (374) is swept proximally to promote proximal deflection of upright leg (374) upon initial contact with pivot pin (350) as the proximal ends of cartridge half (302) and anvil half (304) are brought together, as described below. While in the present example retaining spring (370) is secured to cartridge channel member (306) and pivot pin (350) is secured to anvil channel member (340), a reverse configuration may be provided in other examples.

B. Exemplary Method of Coupling Halves of Linear Cutting Stapler

FIG. 13A shows cartridge half (302) and anvil half (304) separated from one another and positioned in alignment for coupling together, with latching lever (322) pivoted away from cartridge channel member (306) in its open position. In this open position of lever (322), jaws (328) are oriented such that the open distal ends of their elongate slots (330) are positioned in alignment with opposing ends of latch pin (354). Additionally, pivot pin (350) of anvil half (304) is positioned in alignment with proximal flange slots (320) of cartridge channel member (306).

As shown in FIGS. 13B and 14, the proximal ends of cartridge half (302) and anvil half (304) are brought together so that the proximal end of anvil channel member (340) is received between proximal side flanges (318) of cartridge channel member (306), and proximal pivot pin (350) is directed into proximal flange slots (320). Upon entering proximal flange slots (320) of cartridge channel member (306), pivot pin (350) engages swept free end (376) of retaining spring (370) and forces upright leg (374) of spring (370) to deflect proximally. Pivot pin (350) is then received and captured within recess (378) of retaining spring (370), thereby coupling together the proximal ends of cartridge half (302) and anvil half (304). Meanwhile, as shown in FIG. 13B, latching lever (322) remains in the open position such that anvil half (304) may pivot relative to cartridge half (302) about the pivot axis defined by proximal pivot pin (350). In that regard, pivot pin (350) is permitted to rotate within recess (378) of retaining spring (370). Additionally, with latching lever (322) in the open position, opposed ends of latch pin (354) are received within the open distal ends of jaw slots (330).

When proximal pivot pin (350) of anvil half (304) is coupled with retaining spring (370) of cartridge half (302) as described above, upright leg (374) of spring (370) is configured to exert a distally directed spring force on pivot pin (350). This spring force is sufficient to keep the proximal ends of the instrument halves (302, 304) coupled together unless an operator applies a minimum transverse separation force on instrument halves (302, 304) to intentionally separate halves (302, 304). Retaining spring (370) may be provided with any suitable stiffness so that upright leg (374)

deflects proximally to release pivot pin (350) from recess (378), and thereby permit separation of instrument halves (302, 304), upon the application of a selected minimum transverse separation force on instrument halves (302, 304). Advantageously, this configuration enables the operator to manipulate stapler (300) with a single hand once halves (302, 304) are coupled together at their proximal ends, while leaving the other hand free to position tissue relative to staple cartridge (312) and anvil plate (346). Because the proximal ends of halves (302, 304) remain coupled together, lever jaws (328) remain properly aligned with latch pin (354) such that the operator may easily close latching lever (322) single-handedly once the tissue is suitably positioned relative to stapler (300).

Figure 15:
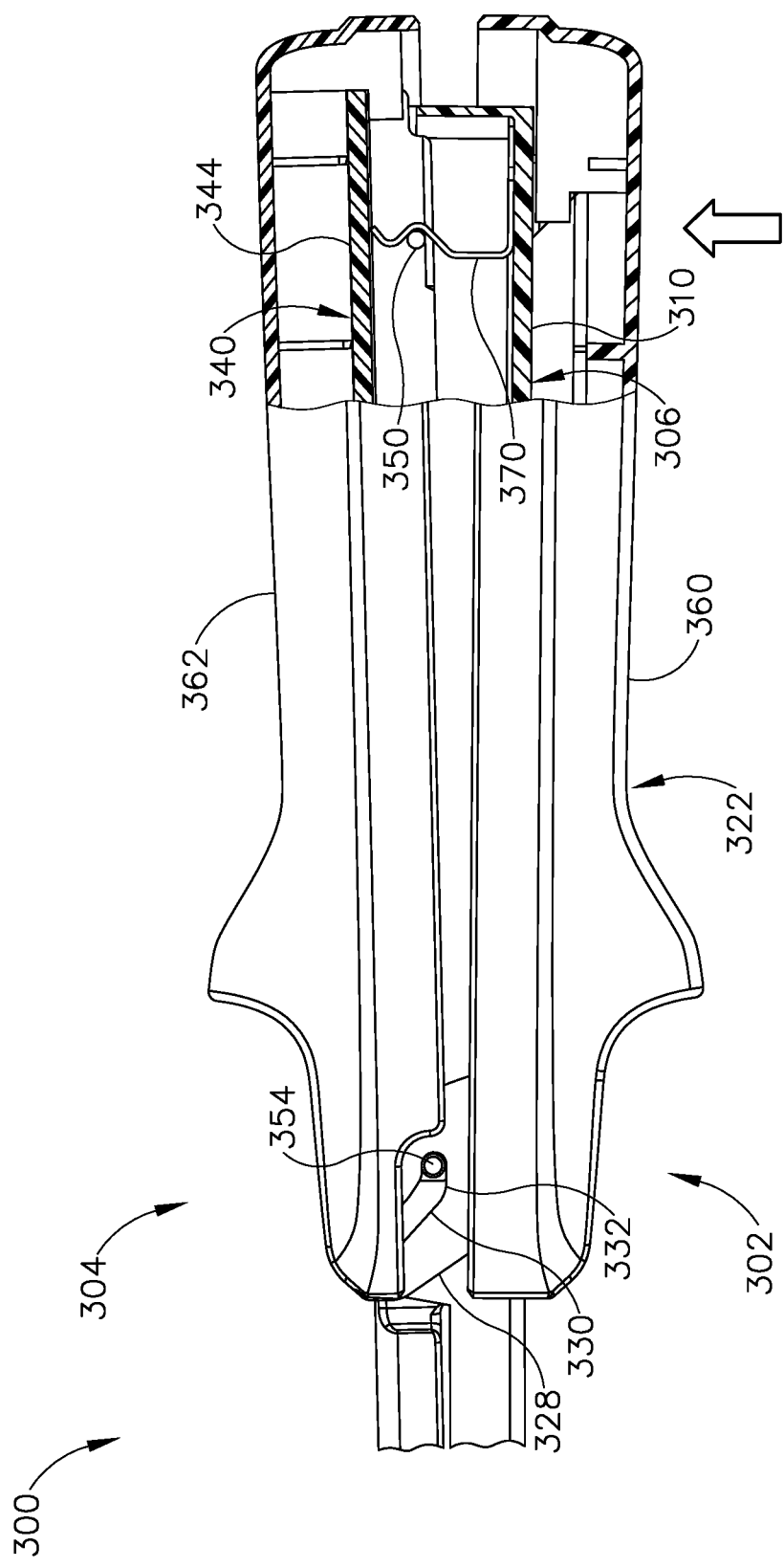
FIG. 15 depicts a partial cross-sectional side view of the surgical stapling instrument of FIG. 13B, showing the instrument halves coupled together in a closed position.

As shown in FIG. 15, latching lever (322) is pivoted toward cartridge channel member (306) to its closed position to thereby lock anvil half (304) against cartridge half (302), and to securely clamp tissue between staple cartridge (312) and anvil plate (346). As latching lever (322) is pivoted closed, an upper edge of each jaw slot (330) cams against a side surface of the respective end of latch pin (354), thereby drawing latch pin (354) proximally through jaw slots (330) and causing anvil half (304) to pivot toward cartridge half (302) about proximal pivot pin (350). As latching lever (322) reaches its fully closed position, the ends of latch pin (354) are captured within proximal slot portions (332) of jaw slots (330) and against their closed proximal ends, thereby locking anvil half (304) to cartridge half (302) such that anvil channel member (340) is fixed relative to cartridge channel member (306). Subsequently, the firing assembly (not shown) of stapler (300) may be activated by the operator in a manner similar to that described above in connection with firing assembly (200), to thereby cut and staple the tissue simultaneously. After returning a firing knob (not shown) of the firing assembly to its proximal position, the tissue may then be released from stapler (300) by opening latching lever (322) and separating instrument halves (302, 304) from one another.

III. Exemplary Linear Cutting Stapler Having Swingarm Link

As described above, first and second halves (302, 304) of stapler (300) are releasably coupled together at their proximal ends, such that halves (302, 304) are longitudinally fixed yet pivotable relative to one another when the latching lever is in the open position. In some instances, it may be desirable to provide a configuration in which the stapler halves remain coupled together when the latching lever is in an open position, but where the stapler halves are movable longitudinally relative to one another to further facilitate positioning of the stapler relative to tissue. The exemplary stapler (400) described below includes features that provide this functionality.

Figure 16A:
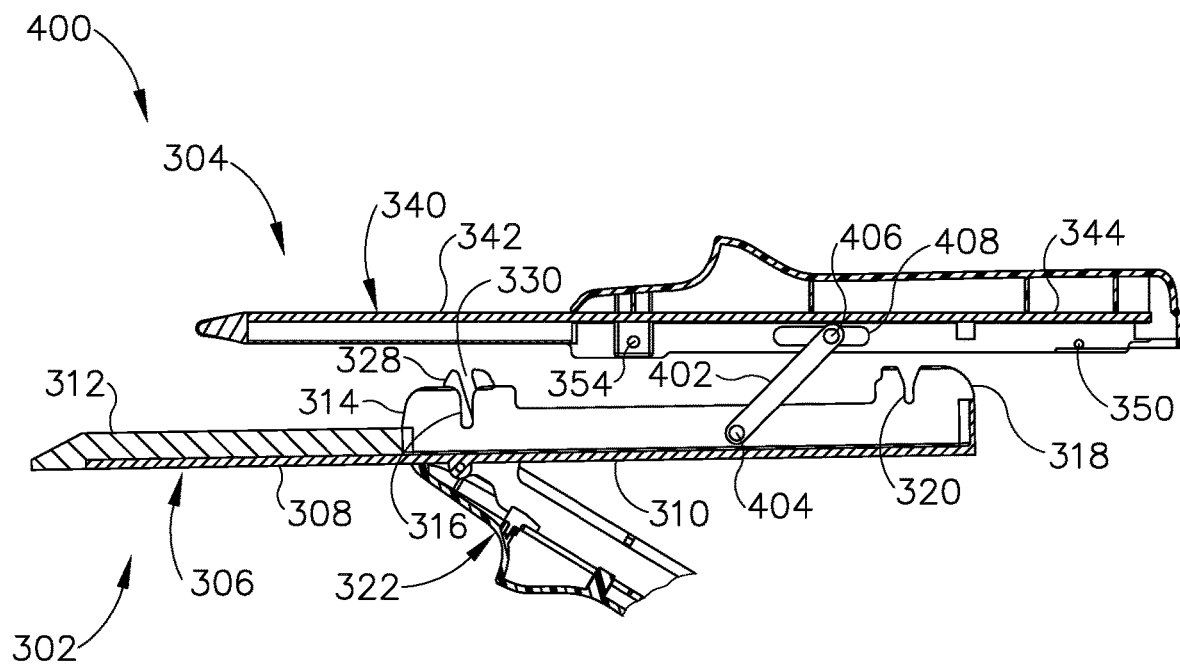
FIG. 16A depicts a cross-sectional side view of another exemplary surgical stapling instrument having a swing arm that couples together an anvil half and a cartridge half of the instrument, showing the instrument halves arranged in a first position.
Figure 16B:
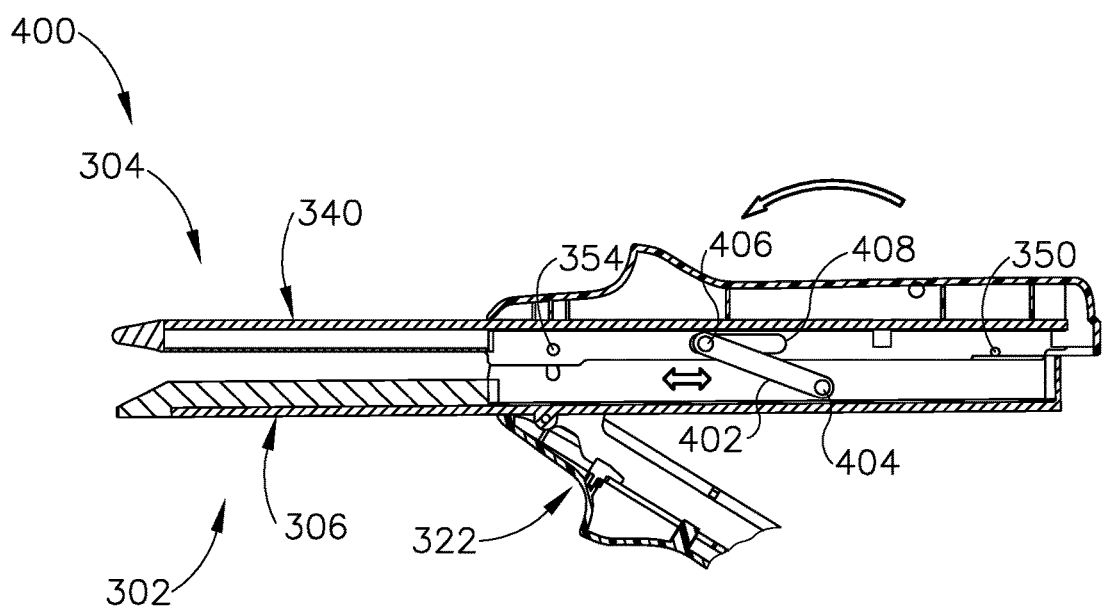
FIG. 16B depicts a cross-sectional side view of the surgical stapling instrument of FIG. 16A, showing the instrument halves arranged in a second position.

FIGS. 16A and 16B show another exemplary linear cutting stapler (400) for which like reference numerals refer to like features of stapler (300) described above. In that regard, stapler (400) is similar to stapler (300) except as otherwise described below. Stapler (400) is different from stapler (300) in that stapler (400) omits proximal retaining spring (370) and includes a swingarm link (402) that movably couples cartridge half (302) with anvil half (304). A first end of swingarm link (402) is pivotably coupled with proximal frame portion (310) of cartridge channel member (306) by a first swingarm pivot pin (404). A second end of swingarm link (402) is pivotably coupled with proximal frame portion (344) of anvil channel member (340) by a second swingarm pivot pin (406). In the present example, anvil channel member (340) includes a longitudinally extending slot (408) formed in one or both of opposing sidewalls of proximal frame portion (344). Second swingarm pivot pin (406) is slidably received within the one or more longitudinal slots (408) and is configured to translate proximally and distally within slots (408) relative to anvil channel member (340). It will be appreciated that slots (408) are merely optional, and may be omitted from stapler (400). In other versions, slots (408) may be provided in proximal frame portion (310) of cartridge channel member (306).

Swingarm link (402) is configured to facilitate transitioning of instrument halves (302, 304) between a disengaged position shown in FIG. 16A, and an engaged position shown in FIG. 16B, while keeping halves (302, 304) coupled to one another such that stapler (400) can be held single-handedly by an operator. In the disengaged position shown in FIG. 16A, anvil half (304) is positioned proximal relative to cartridge half (302). Additionally, instrument halves (302, 304) are spaced apart from one another transversely such that latching lever (322) of cartridge half (302) is disengaged from latch pin (354) of anvil half (304), and such that proximal pin (350) of anvil half (304) is disengaged from proximal flange slots (320) of cartridge half (302). In this disengaged position, the operator is able to hold stapler (400) with a first hand, and manipulate tissue relative to instruments halves (302, 304) with a second hand. Additionally, anvil half (304) may be translated relative to cartridge half (302) via longitudinal slots (408) to facilitate alignment of tissue with stapler (400). Accordingly, swingarm link (402) facilitates proper alignment of instruments halves (302, 304) with one another during use.

While only one swingarm link (402) is shown in the present example, positioned centrally relative to proximal frame portions (310, 344) of cartridge and anvil channel members (306, 340), two or more swingarm links (402) may be provided in other examples. For instance, a first swingarm link (402) may be positioned at a proximal end of proximal frame portions (310, 344), and a second swingarm link (402) may be positioned at a distal end of proximal frame portions (310, 344). It will be appreciated that stapler (400) may additionally include various other features of stapler (100) described above in other versions.

To transition instrument halves (302, 304) to the engaged position shown in FIG. 16B, anvil half (304) is advanced distally relative to cartridge half (302) so that swingarm link (402) swings distally through an arc by pivoting relative to instrument halves (302, 304) at first and second swingarm pivot pins (404, 406). Simultaneously, second pivot pin (406) may translate within longitudinal slots (408) of anvil channel member (340) to facilitate this transition. Cartridge half (302) and anvil half (304) may remain generally parallel to one another while transitioning between the disengaged and engaged positions. In the engaged position, opposed ends of latch pin (354) are received within the open distal ends of jaw slots (330) of latching lever (322), and proximal pin (350) is received within proximal flange slots (320). To fully close stapler (400) and clamp tissue positioned between staple cartridge (312) and anvil plate (346), latching lever (322) may be pivoted from the open position to the closed position in the manner described above in connection with stapler (300).

IV. Exemplary Linear Cutting Stapler Having Scissor Configuration

In some instances, it may be desirable for the first and second halves of a stapler to remain parallel to one another while being transitioned between open and closed configurations during a surgical procedure. The exemplary stapler (500) described below includes features that provide this functionality.

Figure 17A:
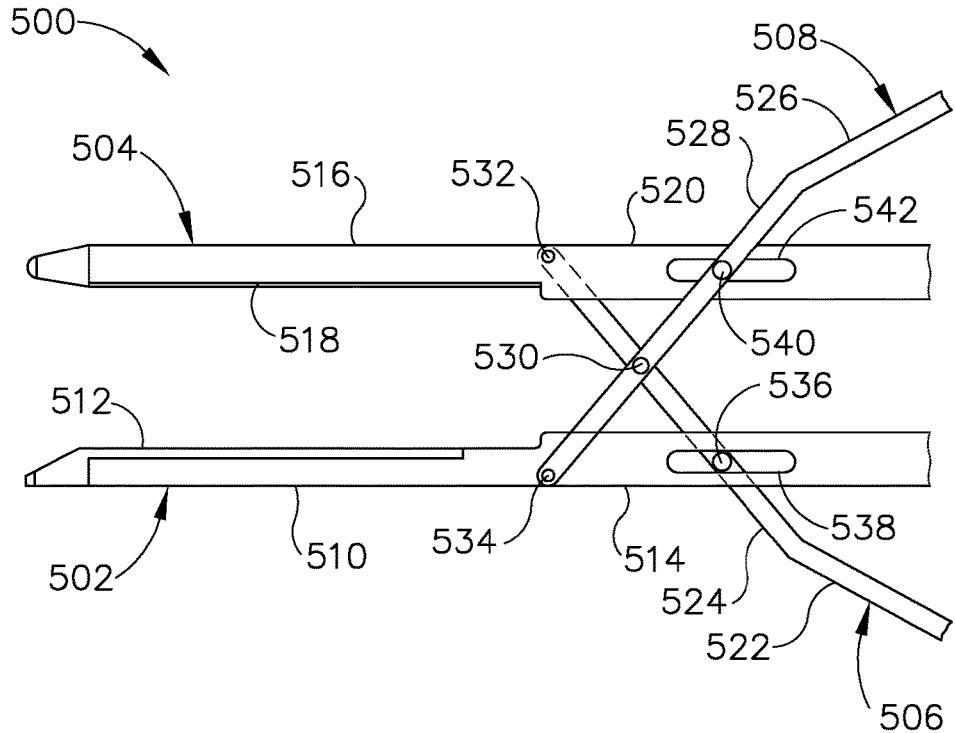
FIG. 17A depicts a side elevational view of another exemplary surgical stapling instrument having first and second halves coupled together in a scissor-like configuration, showing the first and second halves arranged in a first position.
Figure 17B:
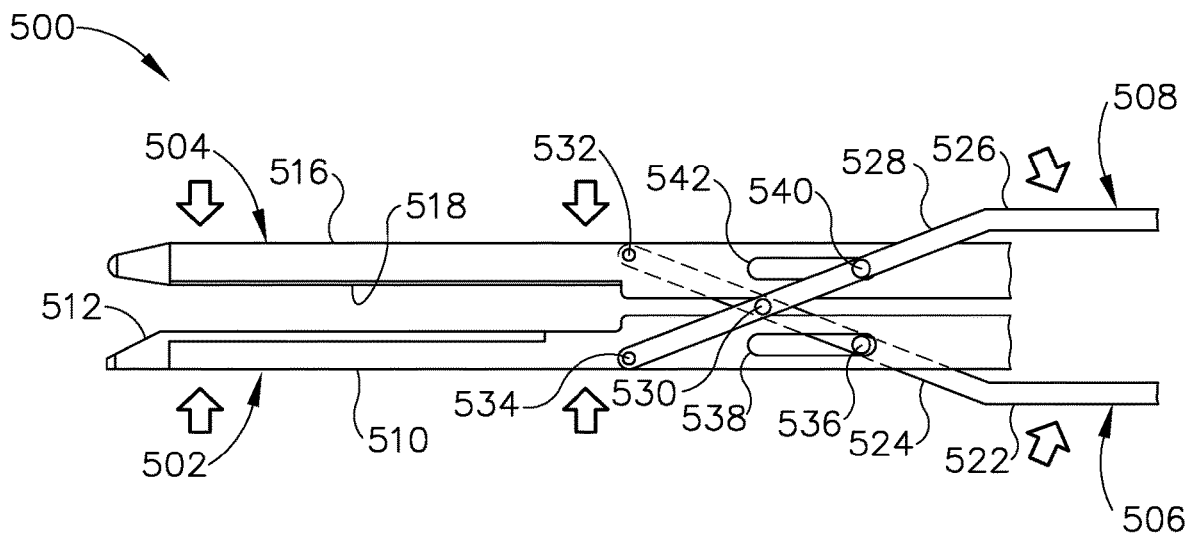
FIG. 17B depicts a side elevational view of the surgical stapling instrument of FIG. 17A, showing the first and second halves arranged in a second position.

FIGS. 17A and 17B show another exemplary linear cutting stapler (500) having a cartridge channel member (502), an anvil channel member (504), a first clamping lever (506), and a second clamping lever (508) coupled together in a scissor-like configuration. Cartridge channel member (502) is similar to cartridge channel member (306) in that cartridge channel member (502) has a distal channel portion (510) configured to receive a staple cartridge (512), which may be similar to staple cartridge (150) described above, and a proximal frame portion (514) configured to slidably receive a firing assembly (not shown) similar to firing assembly (200) described above. Anvil channel member (504) is similar to anvil channel member (340) in that anvil channel member (504) has a distal channel portion (516) that supports an anvil surface in the form of anvil plate (518), and a proximal frame portion (520).

First clamping lever (506) includes a first proximal handle segment (522) and a first distal actuating segment (524) extending angularly relative to first handle segment (522). Similarly, second clamping lever (508) includes a second proximal handle segment (526) and a second distal actuating segment (528) extending angularly relative to second handle segment (526). First and second actuating segments (524, 528) are pivotably coupled together at central portions thereof by a stationary central pivot pin (530). A distal end of first actuating segment (524) is pivotably coupled to proximal frame portion (520) of anvil channel member (504) with a first fixed pivot pin (532). A distal end of second actuating segment (528) is pivotably coupled to proximal frame portion (514) of cartridge channel member (502) with a second fixed pivot pin (534). A proximal portion of first actuating segment (524) is pivotably and slidably coupled to proximal frame portion (514) of cartridge channel member (502) with a first sliding pivot pin (536) arranged within a first longitudinal slot (538) formed in proximal frame portion (514). A proximal portion of second actuating segment (528) is pivotably and slidably coupled to proximal frame portion (520) of anvil channel member (504) with a second sliding pivot pin (540) arranged within a second longitudinal slot (542) formed in proximal frame portion (520). It will be appreciated that stapler (500) may include various additional features of staplers (100, 300, 400) described above.

Cartridge channel member (502) and anvil channel member (504) are transitioned between an open position shown in FIG. 17A and a closed position shown in FIG. 17B by moving clamping levers (506, 508). In particular, an operator draws first and second handle segments (522, 526) together to place channel members (502, 504) in the closed position, and pulls handle segments (522, 526) apart to place channel members (502, 504) in the open position. As the operator moves handle segments (522, 526) relative to one another, clamping levers (506, 508) pivot relative to one another about central pivot pin (530). Simultaneously, first clamping lever (506) pivots relative to anvil channel member (504) about first fixed pivot pin (532), and swings relative to cartridge channel member (502) via translation of first sliding pivot pin (536) within first longitudinal slot (538). Simultaneously, second clamping lever (508) pivots relative to cartridge channel member (502) about second fixed pivot pin (534), and swings relative to anvil channel member (504) via translation of second sliding pivot pin (540) within second longitudinal slot (542). As a result, cartridge and anvil channel members (502, 504) move transversely toward and away from one another while remaining parallel to one another.

Advantageously, this promotes application of equal clamping pressure to tissue along a length of staple cartridge (512) and anvil plate (518), as well as proper alignment of staple cartridge (512) and anvil plate (518) with one another during use.

V. Exemplary Linear Cutting Stapler Having Fixed Proximal Pivot Pin

In some instances, it may be desirable for the first and second halves of a stapler to remain coupled together in a non-releasable manner through a surgical procedure. The exemplary stapler (600) described below includes features that provide this functionality.

Figure 18A:
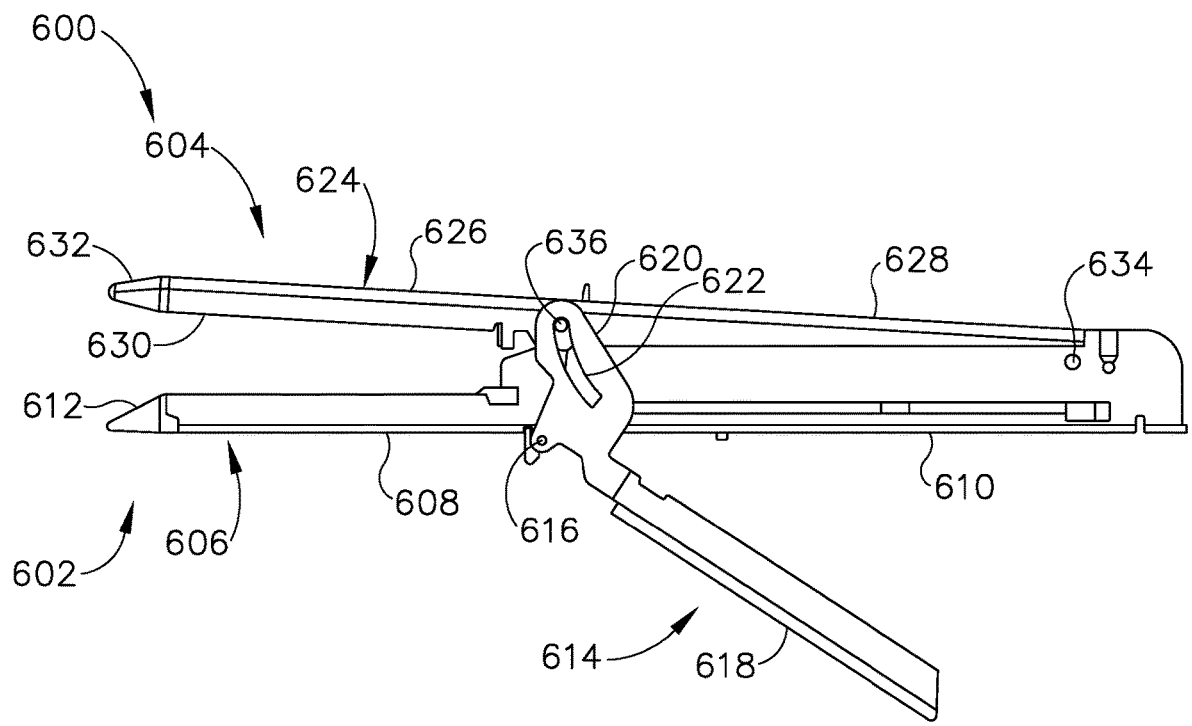
FIG. 18A depicts a side elevational view of another exemplary surgical stapling instrument, showing first and second halves of the instrument in a first position.
Figure 18B:
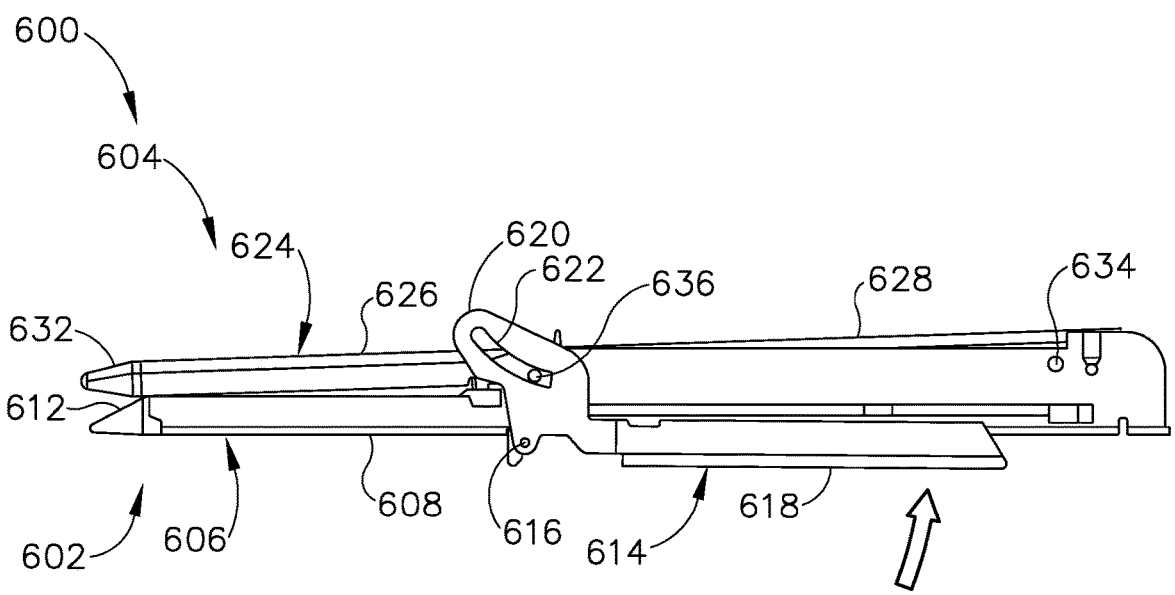
FIG. 18B depicts a side elevational view of the surgical stapling instrument of FIG. 18A, showing the first and second halves in a second position.

FIGS. 18A and 18B show another exemplary linear cutting stapler (600). Stapler (600) is similar to staplers (100, 300) in that stapler (600) includes a cartridge half (602) and an anvil half (604). Cartridge half (602) includes an elongate cartridge channel member (606) having a distal channel portion (608) and a proximal frame portion (610). Distal channel portion (608) is configured to receive a staple cartridge (612), which may be similar to staple cartridge (150) described above. Proximal frame portion (610) is configured to slidably house the components of a firing assembly (not shown), which may be similar to firing assembly (200) described above. A latching lever (614) is pivotably coupled to cartridge channel member (606) with a latch pivot pin (616) arranged at a medial portion of cartridge channel member (606). Latching lever (614) includes an elongate lever arm (618) and a pair of opposed jaws (620) extending distally from lever arm (618). Each jaw (620) includes an elongate slot (622) configured to receive a corresponding latch projection of anvil half (604), as described below. Each jaw slot (622) is closed at its proximal and distal ends, thereby retaining the corresponding latch projection within jaw slot (622).

Anvil half (604) of stapler (600) includes an elongate anvil channel member (624) having a distal channel portion (626) and a proximal frame portion (628). Distal channel portion (626) supports an anvil surface in the form of anvil plate (630), which may be similar to anvil plate (346) described above, and a distal tip member (632). Proximal frame portion (628) of anvil channel member (624) is configured to be received between opposed sidewalls of proximal frame portion (628) of cartridge channel member (606).

Stapler (600) is different from staplers (100, 300) in that cartridge half (602) and anvil half (604) are configured to remain coupled together throughout all stages of use during a surgical procedure, and are not intended to be separated from one another during the procedure. In that regard, proximal frame portions (610, 628) of cartridge and anvil channel members (606, 624) are pivotably coupled to one another with a laterally extending pivot pin (634) arranged at the proximal ends of channel members (606, 624). Unlike pivot pin (350), pivot pin (634) is captured within bores formed in the sidewalls of proximal frame portions (610, 628) such that pivot pin (616) is fixed relative to channel members (606, 624). Accordingly, the proximal ends of channel members (606, 624) remain pivotably coupled together throughout use of stapler (600) during a surgical procedure, thereby enabling an operator to manipulate stapler (600) with a single hand while ensuring that channel members (606, 624) remain properly aligned with one another during use.

Anvil half (604) further includes a pair of latch projections defined by a laterally extending latch pin (636) coupled to a proximal end of proximal frame portion (628) of anvil channel member (624). Opposed ends of latch pin (636) are captured within jaw slots (622) of latching lever (614). As seen in FIGS. 18A and 18B, latching lever (614) is pivotable relative to channel members (606, 624) between open and closed position for selectively clamping channel members (606, 624) against one another. FIG. 18A shows latching lever (614) in an open position in which latch pin (636) abuts the distal ends of jaw slots (622), and in which staple cartridge (612) and anvil plate (630) are transversely spaced apart from one another to permit manipulation of tissue relative to stapler (600). FIG. 18B shows latching lever (614) in a closed position in which latch pin (636) abuts the proximal ends of jaw slots (622), and in which staple cartridge (612) and anvil plate (630) are clamped against one another so that tissue held therebetween may be simultaneously stapled and cut. It will be appreciated that stapler (600) may include various additional features of staplers (100, 300, 400, 500) described above.

VI. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler, comprising: (a) an anvil half comprising: (i) an anvil channel member, and (ii) an anvil surface having a plurality of staple forming pockets; (b) a cartridge half configured to releasably couple with the anvil half, wherein the cartridge half comprises: (i) a cartridge channel member having a distal portion configured to receive a staple cartridge, and (ii) a latching member movably coupled to the cartridge channel member, wherein the latching member is movable between a closed position in which the latching member fixes the anvil channel member relative to the cartridge channel member, and an open position in which the latching member permits movement of the anvil channel member relative to the cartridge channel member; (c) a resilient member arranged at a proximal end of one of the anvil half or the cartridge half; and (d) a projection arranged at a proximal end of the other of the anvil half or the cartridge half, wherein the resilient member is configured to contact and releasably couple with the projection to thereby couple the proximal end of the anvil half with the proximal end of the cartridge half while the latching member is in the open position.

Example 2

The surgical stapler of Example 1, wherein the resilient member is arranged at a proximal end of the cartridge half, wherein the projection is arranged at a proximal end of the anvil half.

Example 3

The surgical stapler of Example 2, wherein the resilient member is secured to a proximal end of the cartridge channel member.

Example 4

The surgical stapler of any of the preceding Examples, wherein the resilient member is secured to an inner base surface of the cartridge channel member.

Example 5

The surgical stapler of any of the preceding Examples, wherein the resilient member comprises an L-shaped spring having a base leg and an upright leg extending away from the base leg.

Example 6

The surgical stapler of Example 5, wherein the upright leg includes a recess configured to releasably capture the projection.

Example 7

The surgical stapler of any of Examples 5 through 6, wherein the L-shaped spring is secured to a proximal end of the cartridge channel member, wherein the projection is secured to a proximal end of the anvil channel member.

Example 8

The surgical stapler of any of Examples 5 through 7, wherein a free terminal end of the upright leg is configured to confront an inner base surface of the anvil channel member when the projection is coupled to the L-shaped spring.

Example 9

The surgical stapler of any of the preceding Examples, wherein the anvil half is configured to pivot relative to the cartridge half about a pivot axis defined by the projection.

Example 10

The surgical stapler of any of the preceding Examples, wherein the projection is configured to rotate relative to the resilient member when the projection and the resilient member are coupled together.

Example 11

The surgical stapler of any of the preceding Examples, wherein the latching member comprises a latching lever pivotably coupled to the cartridge channel member.

Example 12

The surgical stapler of Example 11, wherein the anvil half includes a latch projection, wherein the latching lever includes a jaw having an elongate slot configured to receive the latch projection.

Example 13

The surgical stapler of Example 12, wherein the elongate slot is configured to receive the latch projection in each of the open and closed positions of the latching lever while the proximal ends of the anvil and cartridge halves are coupled together.

Example 14

The surgical stapler of any of the preceding Examples, wherein the anvil channel member includes a distal channel portion that supports the anvil surface and a proximal frame portion that supports the projection, wherein the cartridge channel member includes a distal channel portion configured to receive a staple cartridge and a proximal frame portion that supports the resilient member.

Example 15

The surgical stapler of any of the preceding Examples, wherein the projection comprises a laterally extending pin.

Example 16

A surgical stapler, comprising: (a) an anvil half comprising: (i) an anvil channel member, (ii) an anvil surface having a plurality of staple forming pockets, and (iii) a pivot projection coupled to a proximal end of the anvil half; and (b) a cartridge half configured to releasably couple with the anvil half, wherein the anvil half is configured to pivot relative to the cartridge half about an axis defined by the pivot projection, wherein the cartridge half comprises: (i) a cartridge channel member having a distal portion configured to receive a staple cartridge, (ii) a latching member movably coupled to the cartridge channel member, wherein the latching member is movable between a closed position in which the latching member fixes the anvil channel member relative to the cartridge channel member, and an open position in which the latching member permits movement of the anvil channel member relative to the cartridge channel member, and (iii) a retaining member coupled to a proximal end of the cartridge half, wherein the retaining member is configured to contact and releasably retain the pivot projection to thereby couple the proximal end of the anvil half with the proximal end of the cartridge half while the latching member is in the open position.

Example 17

The surgical stapler of Example 16, wherein the pivot projection is secured to a proximal end of the anvil channel member, wherein the retaining member is secured to a proximal end of the cartridge channel member.

Example 18

The surgical stapler of any of Examples 16 through 17, wherein the retaining member comprises a resilient member configured to releasably capture the pivot projection.

Example 19

A surgical stapler, comprising: (a) an anvil half comprising: (i) an anvil channel member, (ii) an anvil surface having a plurality of staple forming pockets, and (iii) a latch projection; (b) a cartridge half configured to releasably couple with the anvil half, wherein the cartridge half comprises: (i) a cartridge channel member having a distal portion configured to receive a staple cartridge, and (ii) a latching lever pivotably coupled to the cartridge channel member, wherein the latching lever includes a jaw having an elongate slot, wherein the latching lever is pivotable between a closed position in which the latching lever fixes the anvil channel member relative to the cartridge channel member, and an open position in which the latching lever permits movement of the anvil channel member relative to the cartridge channel member, wherein the latch projection is received within the elongate slot in each of the open and closed positions; and (c) a retaining member coupled to a proximal end of one of the anvil half or the cartridge half, wherein the retaining member is configured to contact and releasably retain a proximal portion of the other of the anvil half or the cartridge half to thereby couple the proximal end of the anvil half with the proximal end of the cartridge half while the latching lever is in the open position.

Example 20

The surgical stapler of Example 19, wherein the retaining member comprises a spring.

VII. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on even date herewith, issued as U.S. Pat. No. 10,631,866 on Apr. 28, 2020; U.S. application Ser. No. 15/889,370, entitled "Lockout Assembly for Linear Surgical Stapler," filed on even date herewith, issued as U.S. Pat. No. 10,667,818 on Jun. 2, 2020; U.S. application Ser. No. 15/889,376, entitled "Releasable Coupling Features for Proximal Portions of Linear Surgical Stapler," filed on even date herewith, issued as U.S. Pat. No. 10,898,197 on Jan. 26, 2021; U.S. application Ser. No. 15/889,388, entitled "Firing Lever Assembly for Linear Surgical Stapler," filed on even date herewith, issued as U.S. Pat. No. 10,874,398 on Dec. 29, 2020; and U.S. application Ser. No. 15/889,390, entitled "Clamping Mechanism for Linear Surgical Stapler," filed on even date herewith, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler, comprising:
   (a) an anvil half comprising:
      (i) an anvil channel member, and
      (ii) an anvil surface having a plurality of staple forming pockets;
   (b) a cartridge half configured to releasably couple with the anvil half, wherein the cartridge half comprises:
      (i) a cartridge channel member having a distal portion configured to receive a staple cartridge, and
      (ii) a latching member movably coupled to the cartridge channel member, wherein the latching member is movable between a closed position in which the latching member fixes the anvil channel member relative to the cartridge channel member, and an open position in which the latching member permits movement of the anvil channel member relative to the cartridge channel member;
   (c) a resilient member arranged at a proximal end of one of the anvil half or the cartridge half and provided separately from the latching member, wherein the resilient member includes a recess that opens in one of a proximal direction or a distal direction; and
   (d) a projection arranged at a proximal end of the other of the anvil half or the cartridge half and provided separately from the latching member,
   wherein the resilient member is configured to contact and releasably retain the projection within the recess to thereby couple the proximal end of the anvil half with the proximal end of the cartridge half while the latching member is in the open position.

2. The surgical stapler of claim 1, wherein the resilient member is arranged at a proximal end of the cartridge half, wherein the projection is arranged at a proximal end of the anvil half.

3. The surgical stapler of claim 2, wherein the resilient member is secured to a proximal end of the cartridge channel member.

4. The surgical stapler of claim 3, wherein the resilient member is secured to an inner base surface of the cartridge channel member.

5. The surgical stapler of claim 1, wherein the resilient member comprises an L-shaped spring having a base leg and an upright leg extending away from the base leg.

6. The surgical stapler of claim 5, wherein the upright leg includes the recess.

7. The surgical stapler of claim 5, wherein the L-shaped spring is secured to a proximal end of the cartridge channel member, wherein the projection is secured to a proximal end of the anvil channel member.

8. The surgical stapler of claim 7, wherein a free terminal end of the upright leg is configured to confront an inner base surface of the anvil channel member when the projection is coupled to the L-shaped spring.

9. The surgical stapler of claim 1, wherein the anvil half is configured to pivot relative to the cartridge half about a pivot axis defined by the projection.

10. The surgical stapler of claim 1, wherein the projection is configured to rotate relative to the resilient member when the projection and the resilient member are coupled together.

11. The surgical stapler of claim 1, wherein the anvil half includes a latch projection, wherein the latching member comprises a latching lever that includes a jaw having an elongate slot configured to receive the latch projection.

12. The surgical stapler of claim 1, wherein the anvil channel member includes a distal channel portion that supports the anvil surface and a proximal frame portion that supports the projection, wherein the cartridge channel member includes a distal channel portion configured to receive a staple cartridge and a proximal frame portion that supports the resilient member.

13. The surgical stapler of claim 1, wherein the projection comprises a laterally extending pin.

14. A surgical stapler, comprising:
(a) an anvil half comprising:
   (i) an anvil channel member,
   (ii) an anvil surface having a plurality of staple forming pockets, and
   (iii) a pivot projection coupled to a proximal end of the anvil half; and
(b) a cartridge half configured to releasably couple with the anvil half, wherein the anvil half is configured to pivot relative to the cartridge half about an axis defined by the pivot projection, wherein the cartridge half comprises:
   (i) a cartridge channel member having a distal portion configured to receive a staple cartridge,
   (ii) a latching member movably coupled to the cartridge channel member, wherein the latching member is movable between a closed position in which the latching member fixes the anvil channel member relative to the cartridge channel member, and an open position in which the latching member permits movement of the anvil channel member relative to the cartridge channel member, and
   (iii) a retaining member coupled to a proximal end of the cartridge half, wherein the retaining member includes a recess that opens in one of a proximal direction or a distal direction, wherein the retaining member is configured to contact and releasably retain the pivot projection within the recess to thereby couple the proximal end of the anvil half with the proximal end of the cartridge half while the latching member is in the open position.

15. The surgical stapler of claim 14, wherein the pivot projection is secured to a proximal end of the anvil channel member, wherein the retaining member is secured to a proximal end of the cartridge channel member.

16. The surgical stapler of claim 14, wherein the retaining member comprises a resilient member configured to releasably capture the pivot projection.

17. A surgical stapler, comprising:
(a) an anvil half comprising:
   (i) an anvil channel member,
   (ii) an anvil surface having a plurality of staple forming pockets, and
   (iii) a latch projection;
(b) a cartridge half configured to releasably couple with the anvil half, wherein the cartridge half comprises:
   (i) a cartridge channel member having a distal portion configured to receive a staple cartridge, and
   (ii) a latching lever pivotably coupled to the cartridge channel member, wherein the latching lever includes a latching jaw having an elongate slot, wherein the elongate slot comprises:
      (A) an open distal end,
      (B) a first linear slot portion extending proximally from the open distal end,
      (C) a second linear slot portion extending proximally from and angularly relative to the first linear slot portion, and
      (D) a closed proximal end,
   wherein the latching lever is pivotable between a closed position in which the latching lever fixes the anvil channel member relative to the cartridge channel member, and an open position in which the latching lever permits movement of the anvil channel member relative to the cartridge channel member, wherein the latching jaw is configured to receive the latch projection within the first linear slot portion in the open position and within the second linear slot portion in the closed position; and
(c) a retaining member coupled to a proximal end of one of the anvil half or the cartridge half, wherein the retaining member is configured to contact and releasably retain a proximal portion of the other of the anvil half or the cartridge half to thereby couple the proximal end of the anvil half with the proximal end of the cartridge half while the latching lever is in the open position.

18. The surgical stapler of claim 1, wherein the spring includes a free terminal end that projects in one of a proximal direction or a distal direction.

19. The surgical stapler of claim 17, wherein the retaining member includes a recess that opens in one of a proximal direction or a distal direction, wherein the retaining member is configured to releasably retain the proximal portion to thereby couple the proximal end of the anvil half with the proximal end of the cartridge half while the latching lever is in the open position.

20. The surgical stapler of claim 1, wherein the resilient member consists of only one single spring leg that extends toward the other of the anvil half or the cartridge half.

* * * * *